United States Patent [19]

Naruto et al.

[11] Patent Number: 4,613,680
[45] Date of Patent: Sep. 23, 1986

[54] PREPARATION OF ANGELIC ACID OR ESTERS THEREOF

[75] Inventors: Masanobu Naruto; Hisao Kondo, both of Kamakura; Go Hata, Fujisawa, all of Japan

[73] Assignee: Toray Industries, Inc., Tokyo, Japan

[21] Appl. No.: 589,075

[22] PCT Filed: Jun. 28, 1982

[86] PCT No.: PCT/JP82/00248

§ 371 Date: Feb. 24, 1984

§ 102(e) Date: Feb. 24, 1984

[87] PCT Pub. No.: WO84/00161

PCT Pub. Date: Jan. 19, 1984

[51] Int. Cl.$^4$ .................. C07C 67/333; C07C 51/353
[52] U.S. Cl. ........................... 560/205; 560/217; 560/220; 560/221; 562/598; 549/499; 203/38
[58] Field of Search ............. 560/205, 220, 221, 217; 562/598, 591, 601; 260/405.6; 549/499

[56] References Cited

PUBLICATIONS

Toray Industries, Inc. Chemical Abstracts, vol. 97 (1982) #181, 761v and p. 1471CS.
Kirk-Othmer Encyclopedia of Chemical Technology 2nd. Ed. (1965), vol. 8, p. 356.
Gibson, T. W. et al. *J. Org. Chem.*, vol. 41 (1976) pp. 791-793.
*The Merck Index* (1976) 9th Ed., pp. 681 and 9156, Merck & Co., publ.
March, Jerry *Advanced Organic Chemistry*, 2nd Ed. 113-114, (1977).
CRC *Handbook of Chemistry and Physics* (1976-7) 57th Ed., p. C-232 CRC Press.
Nozaki, H. et al. *Tetrahedron*, vol. 23 (1967) pp. 2173-2179.
*Hackh's Chemical Dictionary* (1969) McGraw-Hill, Publ. at p. 681.

*Primary Examiner*—Natalie Trousof
*Assistant Examiner*—L. Hendriksen
*Attorney, Agent, or Firm*—Austin R. Miller

[57] ABSTRACT

Angelic acid or esters thereof which are useful as perfume materials are prepared by isomerizing tiglic acid or an ester thereof with an organic sulfinic acid as the catalyst, and novel esters of angelic acid represented by the formula

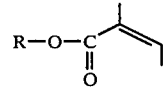

wherein R represents 3-hexenyl, 3-methyl-2-butenyl, 3-methyl-3-butenyl, 3-methyl-2-pentenyl, 3-methyl-4-pentenyl, $CH_3(CH_2)_l$- (in which l is an integer from 5 to 9), cyclopentyl, cyclohexyl, 2-methylpentyl, α-methylbenzyl, neryl or furfuryl are provided as part of said esters of angelic acid.

11 Claims, No Drawings

PREPARATION OF ANGELIC ACID OR ESTERS THEREOF

FIELD

The present invention relates to preparation of angelic acid or esters thereof. More particularly, it is concerned with angelic acid or esters thereof, perfume compositions and novel esters of angelic acid.

BACKGROUND

Angelic acid is a known compound which is chemically (Z)-2-methyl-2-butenoic acid and is represented by the formula

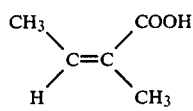

Angelic acid and a part of its esters are contained in natural essential oils, especially in essential oil of chamomile flower in a higher content, are fragrant as they are and are useful as perfume materials.

However, no proposal has been made for the synthetic method of these materials suitable for practical use.

It is an object of this invention to provide a process for preparing angelic acid or esters thereof by simple procedures with formation of by-products inhibited.

Another object of the invention is to provide novel perfume compositions.

A further object of the invention is to provide novel esters of angelic acid.

DISCLOSURE OF THE INVENTION

According to the present invention, angelic acid or esters thereof are prepared by isomerizing tiglic acid or an ester thereof in the presence of an organic sulfinic acid.

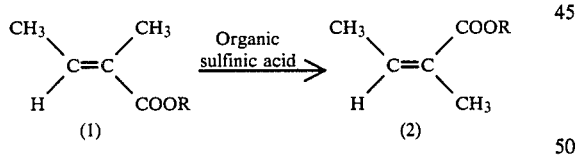

In the above formulae (1) and (2), R is H or an ester radical.

According to the invention, there are also provided perfume compositions containing angelic acid or an ester thereof and novel esters of angelic acid represented by the formulae (3)–(15) below.

(3)
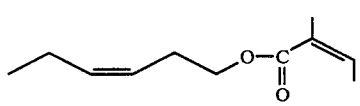

(4)
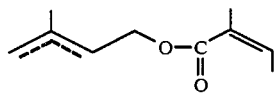

(5)
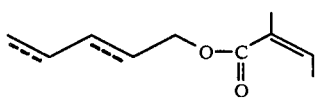

(6)
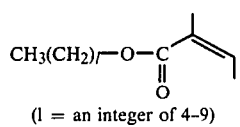

($l$ = an integer of 4–9)

(7)
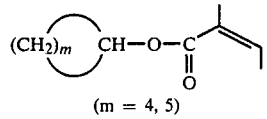

($m$ = 4, 5)

(8)
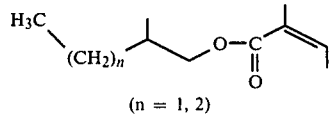

($n$ = 1, 2)

(9)
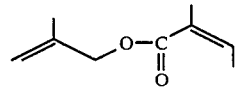

(10)
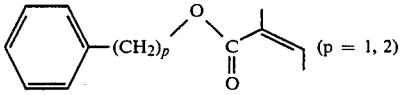 ($p$ = 1, 2)

(11)
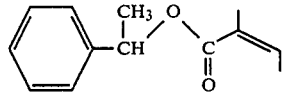

(12)
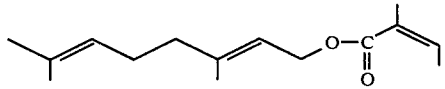

(13)
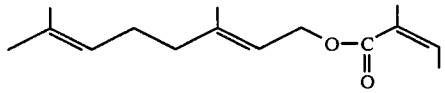

(14)
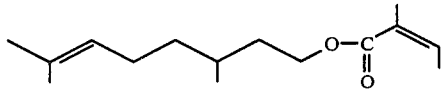

(15)
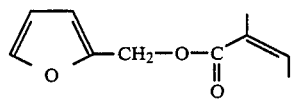

Dotted lines in the above general formulae indicate that a double bond exists on either of the lines.

PREFERRED EMBODIMENTS

Tiglic acid or esters of tiglic acid represented by the general formula (1) which are used as the starting material in the process of the present invention are compounds contained in natural essential oils, for example, in essential oil of gardenia. The compounds are of fragrance per se and are useful as perfume materials. There are also known several processes by which these compounds are chemically prepared. Tiglic acid and certain esters thereof chemically prepared are commercially available. A typical process for the preparation of tiglic acid and esters thereof is described, for example, by R. E. Buckles in Chem. Rev., 55, 659–677 (1955).

These compounds may therefore be made available by known means for the process of the invention.

Their ester radicals in tiglic esters, that is, R in the above-mentioned general formula (1) which in nature do not participate in the reaction may be any one, and it is usually preferred to employ a substituted or unsubstituted saturated or unsaturated hydrocarbon radical containing not more than 20 carbon atoms. As examples of them are mentioned saturated or unsaturated hydrocarbon radicals such as an alkyl group, a cycloalkyl group, an alkenyl group, a cycloalkenyl group or an aralkyl group or substituted hydrocarbon radicals containing, for example, a hydroxyl group, an alkoxy group or an ester group.

As examples of the esters of tiglic acid used in the process of the invention are mentioned, but not limited to, the methyl ester, the ethyl ester, the n-butyl ester, the iso-butyl ester, the sec-butyl ester, the n-amyl ester, the iso-amyl ester, the neopentyl ester, the 2-methylbutyl ester, the n-hexyl ester, the 3-methylpentyl ester, the 2-methyl-2-propenyl ester, the cis-3-hexenyl ester, the citrogelanyl ester, the neryl ester, the linalyl ester, the citronellyl ester, the 2-methyl-2-butenyl ester, the trans-3-hexenyl ester, the 3-methyl-2-butenyl ester, the β-phenylethyl ester, the α-phenylethyl ester, the furfuryl ester.

Since the process of the invention involves a geometrical isomerization reaction of the double bond, those containing an ester radical capable of forming isomers by the reaction may afford a complex mixture as the reaction product. The lower alkyl esters are particularly preferred due to easiness in the reaction and availability.

The organic sulfinic acid used as the catalyst in the process of the invention is a compound represented by the general formula (16) below. n in the general formula may be any integer not less than 1, and R' is usually a hydrocarbon radical such as an aryl or alkyl group. However, it may contain other functional groups provided that the group does not interfere with the catalytic action.

  (16)

The compounds generally employed are arylsulfinic acids or alkylsulfinic acids. As the arylsulfinic acid are mentioned p-toluenesulfinic acid, benzenesulfinic acid, chlorobenzenesulfinic acid, β-naphthalenesulfinic acid and the like. As the alkylsulfinic acid are mentioned methylsulfinic acid, ethylsulfinic acid, propylsulfinic acid, butylsulfinic acid, pentylsulfinic acid, hexylsulfinic acid, heptylsulfinic acid, octylsulfinic acid, nonylsulfinic acid, decylsulfinic acid, dodecylsulfinic acid, octadecylsulfinic acid, eicosylsulfinic acid and the like. However, any of the organic sulfinic acids that possess the catalytic activity may be employed, and the catalysts are not limited to the above-mentioned examples. Such organic sulfinic acid can be synthesized, for example, by the methods described in J. Am. Chem. Soc., 50, 794 (1928) or J. Am. Chem. Soc., 72, 1215 (1950).

Most preferred organic sulfinic acids for use are p-toluenesulfinic acid and benzenesulfinic acid, which are readily available on the market. They can also be prepared in a convenient manner by neutralization of less expensive commercially available sodium salts of the sulfinic acid. The organic sulfinic acid is used at a concentration from 0.01% to 10% (of the tiglic acid or the ester of tiglic acid present in the reaction system) and more preferably at a concentration from 0.05% to 2%.

The reaction is carried out at a temperature in the range from room temperature to 200° C. More preferably, however, it is carried out at 50° C.–170° C. in consideration of the reaction rate and inactivation of the catalyst.

Whereas the reaction proceeds in a variety of solvents such as saturated hydrocarbon solvents, aromatic hydrocarbon solvents, ether solvents, amide solvents and sulfoxide solvents, it proceeds satisfactorily even in the absence of solvent.

The product finally obtained in the isomerization reaction according to the present invention is a thermal equilibrium mixture. Content of angelic acid or an ester of angelic acid, which is thermally unstable owing to its being of a (Z)-form structure, is lower being not more than 10% of the thermal equilibrium mixture. On the other hand, angelic acid or an ester of angelic acid has a lower boiling point than that of tiglic acid or a corresponding ester of tiglic acid. Taking advantage of that fact, angelic acid or an ester of angelic acid can efficiently be produced by continuously isomerizing tiglic acid or an ester of tiglic acid with an organic sulfinic acid and subjecting the resulting mixture to a continuous distillation operation to isolate the angelic acid or the ester of angelic acid.

As the equilibrium in the reaction vessel is shifted by the distillation of angelic acid or an ester of angelic acid in accordance with the process (isomerization distillation), the isomerization reaction can take place continuously.

It is preferable in this method to have a greater difference in boiling point between tiglic acid or an ester of tiglic acid and angelic acid or a corresponding ester of angelic acid. Besides, advantages in distillation temperature and distillation operation are critical for the choice. In these aspects methyl tiglate is most preferred.

As the boiling point of methyl tiglate is 138°–139° C. and that of the corresponding ester methyl angelate is 128°–129° C., the above-described isomerization-distillation process can be conducted under ordinary pressure. There is no question that the isomerization-distillation process can be carried out with esters of tiglic acid other than methyl tiglate or tiglic acid in the same way by adjusting the degree of reduced pressure to meet the optimal temperature for the reaction.

For the continuous processing of the isomerization reaction in the aforementioned isomerization-distillation reaction, deterioration of the organic sulfinic acid is a problem. In general, it is known that organic sulfinic acids undergo a degradation reaction by heating as shown by the general scheme below to afford a corresponding sulfonic acid and a sulfonic acid thiol ester.

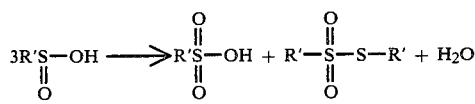

In carrying out the above-described isomerization-distillation, the organic sulfinic acid will also be degraded continuously, and therefore it is required to supply fresh organic sulfinic acid intermittently or continuously when the isomerization-distillation is run for a long period of time. In this case, the amount of organic sulfinic acid to be supplemented will be in the range from 0.01% to 10% and preferably from 0.05% to 0.5% of the tiglic acid or the ester of tiglic acid in the reaction vessel per hour. Although the isomerization-distillation may be carried out in the presence of a solvent as mentioned above, it is done usually and preferably in the absence of solvent.

Tiglic acid or an ester of tiglic acid which is the starting material continuously decreasing in the reaction vessel may also be supplemented continuously or intermittently. It is also feasible to operate a batch system.

The angelic acid or the ester of angelic acid continuously discharged in the aforementioned isomerization-distillation reaction is usually contaminated with the starting material tiglic acid or ester of tiglic acid, purity of the former depending upon the number of plates in the rectifying column.

In order to produce angelic acid or an ester of angelic acid with a higher purity a rectifying column with a number of theoretical plates of not less than 5, preferably from 7 to 30 is employed.

The product thus obtained can further be subjected to conventional rectification to afford angelic acid or an ester of angelic acid of a higher purity.

Angelic acid and esters thereof have a carbonyl group and a conjugated carbon-carbon double bond in their structure. Compounds of this type possibly undergo position isomerization of the double bond if they are treated, for example, with an acidic compound. Unexpectedly, however, there is no position isomerization detectively observed at all in the process of the invention; only geometrical isomerization of the double bond takes place selectively with a surprisingly good reaction ratio on the basis of the catalyst.

In the course of investigations on the preparation of angelic acid and esters thereof we have successfully produced esters of angelic acid having the general formulae (3)-(15) which are unknown in literature and highly effective as a perfume component.

The compound of the general formula (3) heretofore discussed is (Z)-3-hexenyl angelate, compounds of the formula (4) are represented by the following formula (4-a):

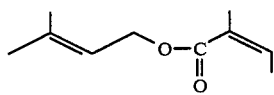
(4-a)

namely 3-methyl-2-butenyl angelate and a compound represented by the following formula (4-b):

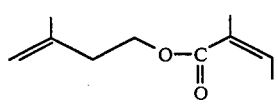
(4-b)

namely 3-methyl-3-butenyl angelate and compounds of the formula (5) are a compound represented by the following formula (5-a):

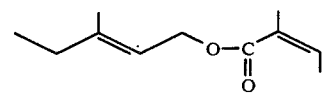
(5-a)

namely 3-methyl-2-pentenyl angelate and a compound represented by the following formula (5-b):

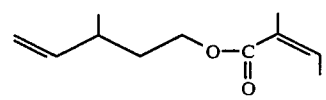
(5-b)

namely 3-methyl-4-pentenyl angelate.

Compounds of the general formula (6) are a compound represented by the following formula (6-a):

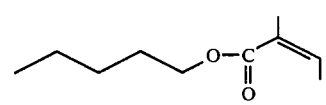
(6-a)

namely n-amyl angelate, a compound represented by the following formula (6-b);

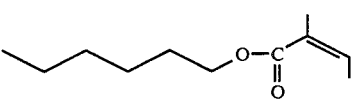
(6-b)

namely n-hexyl angelate, a compound represented by the following formula (6-c):

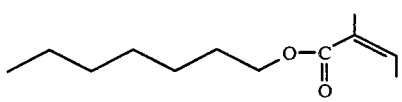
(6-c)

namely n-heptyl angelate, a compound represented by the following formula (6-d):

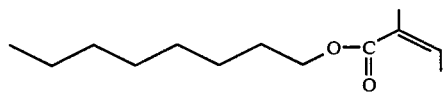
(6-d)

namely n-octyl angelate, a compound represented by the following formula (6-e):

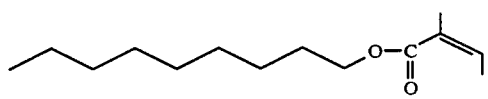
(6-e)

namely n-nonyl angelate and a compound represented by the following formula (6-f):

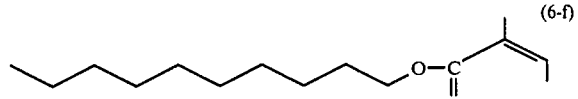
(6-f)

namely n-decyl angelate.

Compounds of the general formula (7) are a compound represented by the following formula (7-a):

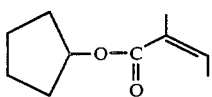
(7-a)

namely cyclopentyl angelate and a compound represented by the following formula (7-b):

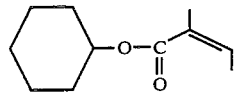
(7-b)

namely cyclohexyl angelate.

Compounds of the formula (8) are a compound represented by the following formula (8-a):

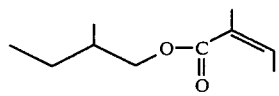
(8-a)

namely 2-methylbutyl angelate and a compound represented by the following formula (8-b):

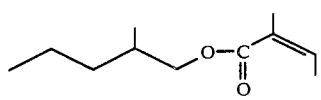
(8-b)

namely 2-methylpentyl angelate and compound of the formula (9) is 2-methylpropenyl angelate.

Compounds of the formula (10) are a compound represented by the following formula (10-a):

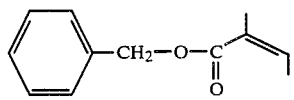
(10-a)

namely benzyl angelate and a compound represented by the following formula (10-b):

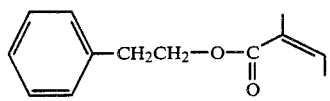
(10-b)

namely β-phenyl angelate.

All of these compounds have excellent aromatic characteristics. It was demonstrated that when one or more of the compounds are incorporated in a perfume composition, an effect unpredictable from each of the compounds alone was produced, and fragrance of the perfume composition was greatly improved.

To describe aromatic characteristics of these compounds in more detail, a compound of the formula (3), namely (Z)-3-hexenyl angelate emits fragrance of strong green note with rosy note as well as of bluish sweetness of perilla grassy and is particularly effective for giving herbal-note, modern chypre and green note of floral bouquet character.

A compound of the formula (4-a), namely 3-methyl-2-butenyl angelate has bergamot-like fragrance with flavor of flower-like green note and is an especially effective perfume material for producing fresh feeling and natural feeling.

In the formulation area, it is especially effective for herbal-type, citrus-note and lavender-note compounding.

A compound of the formula (4-b), namely 3-methyl-3-butenyl angelate is especially effective for giving flower-like natural green note and modifying spicy note.

In the formulation area, it is especially effective as a modifier of ylang-ylang oil and jasmine compounds.

A compound of the formula (5-a), namely 3-methyl-2-pentenyl angelate emits volatile fragrance of metallic green note and is especially effective for inducing natural feeling of jasmone note. It is particularly effective for giving more natural feeling when incorporated in floral-note, green-note and chypre-note perfume formulations.

A compound of the formula (5-b), namely 3-methyl-4-pentenyl angelate has green-note sweetness and dry woody spicy note and is especially effective as a modifier for floral-note and green-note compounds. It produces particularly wonderful effects when incorporated in floral-note and green-note perfume formulations.

Aromatic characteristics of the compounds of the formulae (6)–(15) are as follows:

| | |
|---|---|
| n-Amyl angelate (6-a) | Floral fruity fragrance being fresh and sweet like fruity jasmine. |
| n-Hexyl angelate (6-b) | Very fresh green floral-note fragrance like jasmine and gardenia. |
| n-Heptyl angelate (6-c) | Diffusible, light-top, myrcenol, alcohol C6 and alcohol C8-like green floral-note fragrance. |
| n-Octyl angelate (6-d) | Floral rose-note fragrance with light rose top note like geranyl acetate and citronellyl acetate and fruity residual fragrance like phenylethylisobutyrate. |
| n-Nonyl angelate (6-e) | Rose-note floral green fragrance with particularly good in retainability. |
| n-Decyl angelate (6-f) | Floral green, flower-like spicy fragrance with good retainability. |
| Cyclopentyl angelate (7-a) | Very diffusible, fresh floral green fragrance like jasmone and celery seed. |
| Cyclohexyl angelate (7-b) | Very diffusible, camphor-note fresh green fragrance with a rose oxide-like feature. |
| 2-Methylbutyl angelate (8-a) | Diffusible green floral fragrance with fruity touch |
| 2-Methylpentyl angelate (8-b) | Diffusible rose-note floral fragrance with a apple-note fruity feature. |
| 2-Methylpropenyl angelate (9) | Very diffusible fragrance with herbaceous nuance. |
| Benzyl angelate (10-a) | Slightly heavy, fresh floral fragrance like jasmone. |
| βPhenylethyl angelate (10-b) | Fresh floral, fruity, rose-note durable fragrance with a rose and geranium-like woody feature. |
| α-Methylbenzyl angelate (11) | Slightly floral woody fragrance with a woody rose-note feature. |
| Geranyl angelate (12) | Fragrance with pleasant rose-like aroma and fruity floral, fresh green note. |
| Neryl angelate (13) | Soft floral fragrance with orange sweetness like bergamot. |
| Citrollenyl angelate (14) | Geranium-like mild rosy muguet fragrance. |
| Furfuryl angelate (15) | Unique floral woody amber fragrance associated with sweet smell of burning |

-continued like opoponax or myrrh.

As set forth above, these compounds produce better results when used as a new perfume composition by incorporating in a perfume composition.

Particularly, they produce excellent results when incorporated in a formulated perfume composition for use as cosmetic perfume. They can be used as aromatic compositions (perfuming compositions) by adding to cosmetics (such as soap, ointment, powders, tooth paste, deodorant, shampoo, eau de Cologne and lotion), detergent and the like. They can also be used as flavors by adding to foods, luxuries, bereages and the like. The amount to be incorporated may be varied depending upon the objective and the perfume composition in which they are incorporated and is preferably 0.005–50% by weight, more preferably 0.05–30% by weight of the total weight of the formulated perfume composition.

Where these novel compounds can be produced without question by isomerizing a corresponding ester of tiglic acid, it is preferred that methyl angelate is prepared by the isomerization as described below and then, and a mixture of the angelate and a corresponding alcohol, that is, (Z)-3-hexenyl alcohol, 3-methyl-2-butenol, 3-methyl-3-butenol, 3-methyl-2-pentenyl, 3-methyl-4-pentenol, n-amyl alcohol, n-hexyl alcohol, n-heptyl alcohol, n-octyl alcohol, n-nonyl alcohol, n-decyl alcohol, cyclopentyl alcohol, cyclohexyl alcohol, 2-methylbutyl alcohol, 2-methylpentyl alcohol, 2-methylpropenol, benzyl alcohol, β-phenyletyl alcohol, α-methylbenzyl alcohol, geraniol, nerol, citronellol or furfuryl alcohol is heated in the presence of an ester exchange catalyst.

In general, acids are employed as the ester exchange catalyst, but metal compounds such as organic tin compounds and titanium alkoxides are also employed preferably. Although any solvent which does not adversely affect may be used, non-solvent systems are generally satisfactory. Compounds of the invention are preferred under the same conditions as those for the ester exchange in general.

In the above-described preparative process the reaction proceeds in a better yield when the methanol by-product is distilled off or removed by such means as adsorption on the molecular sieve.

The present invention will be described in more details with reference to examples, which are to be construed as not limiting the scope of the invention in any way.

In the examples below analysis of the reaction product was made by means of gaschromatography.
Instrument used: Shimazu Type GC-3BT
Recorder: Hitachi Type 056
Liquid phase: Reoplex 400 2%
Carrier: Chromosorb GHP
Column: Glass column 3 mm$\phi$×2.1 m
Carrier gas: Helium 60 ml/min
Temperature applied: As given In the above-mentioned gaschromatography, angelic acid or an ester of angelic acid has a lower retaining value than tiglic acid or a corresponding ester of tiglic acid.

Composition ratio of the products was represented as the area ratio as it was recorded by Takeda Rika integrater Type TR-2213.

Reagents employed were commercial ones as they were unless otherwise specified.

EXAMPLE 1

A mixture of 1 g. of methyl tiglate (containing 97.10% of methyl tiglate and 1.68% of methyl angelate) and 10 mg. of p-toluenesulfinic acid was heated at 125° C. for 15 min. After completion of the reaction, the product was analyzed by the above-cited gas-chromatography at a column temperature of 100° C. (the same conditions were used for the analysis of methyl tiglate and methyl angelate hereinbelow) to find that it was an heat equilibrium mixture containing 7.23% of methyl angelate and 90.48% of methyl tiglate.

EXAMPLE 2

To a spinning band rectifying column manufactured by B&R 10 mm in diameter and 800 mm in length (ca. 10 plates) was connected a flask containing 140 g. of methyl tiglate and 100 mg. of p-toluenesulfinic acid. The flask was heated on an oil bath, and distillates were collected at a reflux ratio of around 10–20 and an average distillation rate of 3.75 g. per hour. Temperature at the top of the column was initially 129°–131° C. and was slowly increased with deterioration of the catalyst.

Then, a solution of 1,500 mg. of p-toluenesulfinic acid in 50.2 g. of methyl tiglate was intermittently charged in 15 portions at an interval of 1 hour. Temperature at the top of the column was 130°–132° C. After 16 hours there was obtained 60.0 g. of distillates, which was indicated by gaschromatographic analysis analysis to contain 54.45% of methyl angelate and 42.51% of methyl tiglate.

The distillates were rectified on a spinning band rectifying column Nester Faust Type NFA-200 to obtain methyl angelate with a purity of 94.94%. Said methyl angelate was identified by proton NMR spectrum (in CDCl$_3$ with TMS internal standard) and IR spectrum (liquid film).

Distillation of the liquid remaining in the reaction vessel gave recovery of 118.3 g. of methyl tiglate. It contained 95.97% of methyl tiglate and 3.14% of methyl angelate.

There was remained 12.6 g. of brown liquid in the vessel, which was a mixture of almost pure methyl tiglate and the degradated catalyst with no polymerization observed.

EXAMPLE 3

A mixture of 1 g. of methyl tiglate and 10 mg. of benzenesulfinic acid was heated at 125° C. for 15 min. Gaschromatographic analysis of the reaction product indicated that it was a heat equilibrium mixture containing 7.10% of methyl angelate and 90.60% of methyl tiglate.

EXAMPLE 4

A mixture of 1 g. of tiglic acid (a composition ratio of tiglic acid to angelic acid of 99.38:0.62) and 15 mg. of p-toluenesulfinic acid was heated on an oil bath at 130° C. for 15 min. (During the heating the crystals were molten to a homogeneous solution.) Composition of the mixture after the reaction was a heat equilibrium mixture with a tiglic acid—angelic acid ratio of 96.90:3.10.

EXAMPLE 5

A mixture of 1.0 g. of methyl tiglate, 1.0 ml. of dioxane and 10 mg. of p-toluenesulfinic acid was heated under reflux for 30 min. Gaschromatographic analysis of the reaction product indicated that the composition excluding the dioxane was a heat equilibrium mixture of 7.25% of methyl angelate and 90.16% of methyl tiglate.

EXAMPLE 6

Preparation of 3-methyl-2-butenyl angelate

A mixture of 19.6 g. of methyl angelate, 22.2 g. of 3-methyl-2-butenyl alcohol, 100 ml. of toluene and 1.6 g. of dioctyltin laurate was placed in a glass flask which was equipped with a Soxhlet extractor filled with molecular sieve 4A on the top and a reflux cooler. The mixture was heated under reflux while returning the refluxed liquid through the molecular sieve 4A to the flask. The mixture obtained from the heating for a total of 26 hours was subjected to single distillation to give 24.24 g. of a distillate boiling at 102°–105° C. (25 mmHg).

Purity of the compound was 99.80% as analyzed by gaschromatography (Column: Silicone SE-52, 2%/chromosorb GHP) in terms of the area ratio. The refractive index (D ray, 20° C.) was 1.462. Infrared spectrum had absorptions at 2850–3030, 1715, 1650, 1440, 1380, 1350, 1250, 1225, 1155, 1080, 1040, 960, 845 and 760 cm$^{-1}$.

Proton nuclear magnetic resonance spectrum had absorptions at $\delta = 1.70$–2.02 (m, 12H), 4.64 (d, 2H), 5.40 (m, 1H) and 6.02 (m, 1H) (in deuterochloroform, TMS internal standard).

EXAMPLE 7

Preparation of 3-methyl-3-butenyl Angelate

A mixture of 20.0 g. of methyl angelate, 22.65 g. of 3-methyl-3-butenyl alcohol, 100 ml. of toluene and 0.8 g. of dioctyltin laurate was reacted under the same conditions as in Example 6. The reaction mixture was subjected to single distillation to obtain 39.5 g. of a distillate boiling at 104° C. (32 mmHg).

The distillate was further subjected to rectification to obtain 10.95 g. of a distillate boiling at 100° C. (25 mmHg).

Analysis of the compound by gaschromatography done under the same conditions as in Example 6 indicated a purity of 99.78% in terms of the area ratio. The refractive index (D ray, 20° C.) was 1.454.

Infrared spectrum had absorptions at 3075, 2850–3000, 1715, 1650, 1445, 1380, 1350, 1250, 1150, 1080, 1040, 975, 890, 845 and 750 cm$^{-1}$.

Proton nuclear magnetic resonance spectrum had absorptions at $\delta = 1.70$–2.02 (m, 9H), 2.40 (t, 2H), 4.29 (t, 2H), 4.80 (m, 2H) and 6.06 (m, 1H) (in deuterochloroform, TMS internal standard).

EXAMPLE 8

Lavender-Cologne Perfume Composition

| | % by weight |
|---|---|
| Lavender oil | 7.0 |
| Lavender absolute | 1.5 |
| Bergamot oil | 7.0 |
| Lemon oil | 20.0 |
| Orange oil | 1.0 |
| Verveine oil | 6.0 |
| Eugenol | 2.5 |
| Essence rose Turkey | 0.5 |
| Jasmine absolute | 3.0 |
| Rhodinol pure | 3.0 |
| αHexylcinnamaldehyde | 10.0 |

-continued

| | % by weight |
|---|---|
| Oakmoss absolute | 1.0 |
| Vetiver oil Bourbon | 1.0 |
| Patchouli oil | 2.0 |
| Musk ketone | 7.0 |
| Musquet base | 14.0 |
| Rose base MS/37 | 5.0 |
| Terpenyl acetate | 4.0 |
| Labdanum oil | 2.0 |
| o-tert-Butylcyclohexyl acetate | 2.0 |
| 3-Methyl-2-butenyl angelate | 0.5 |
| Total | 100.0 |

The above-mentioned perfume composition was evaluated by three skilled perfumers as being of increased fresh feeling and improved tone as compared with a reference composition in which no 3-methyl-2-butenyl angelate was incorporated.

EXAMPLE 9

Artificial Ylang-Ylang Oil

| | % by weight |
|---|---|
| Benzyl acetate | 25.0 |
| Linalol | 10.0 |
| Cananga oil Java | 5.0 |
| Methyl benzoate | 5.0 |
| p-Cresyl methyl ester | 5.0 |
| Terpineol | 5.0 |
| p-Cresyl acetate | 5.0 |
| Geraniol | 5.0 |
| Geranyl acetate | 3.0 |
| Methyleugenol | 1.0 |
| Isoeugenol | 1.0 |
| Eugenol | 1.0 |
| Benzyl alcohol | 1.0 |
| Benzyl benzoate | 3.0 |
| Benzyl salicylate | 20.0 |
| Caryophillin | 4.0 |
| 3-Methyl-3-butenyl angelate | 1.0 |
| Total | 100.0 |

The above-mentioned perfume composition was evaluated by three skilled perfumers as being of increased natural feeling and much improved note and strength as compared with a reference composition in which no 3-methyl-3-butenyl angelate was incorporated.

EXAMPLE 10

Preparation of (Z)-3-Hexenyl Angelate

A mixture of 20.0 g. of methyl angelate, 26.34 g. of (Z)-3-hexenyl alcohol, 100 ml. of toluene and 1.2 g. of dioctyltin laurate was placed in a 300 ml. glass flask, which was equipped with a Soxhlet extractor filled on the top with molecular sieve 4A and a reflux cooler.

The above mixture was heated under continuous reflux while returning the refluxed liquid through the molecular sieve 4A to the flask. The mixture resulted from the heating for a total of 26 hours was subjected to single distillation to give 33.10 g. of a distillate boiling at 120° C. (25 mmHg). The distillate was further subjected to rectification to give 8.46 g. of a distillate boiling at 115° C. (22 mmHg). Analysis of the compound by gaschromatography (Column: Silicone SE-52, 2%/chromosorb GHP) indicated a purity of 99.81% in terms of the area ratio. Refractive index (D ray, 20° C.) was 1.456. Infrared spectrum had absorptions at 2870–3020, 1720, 1650, 1455, 1390, 1350, 1255, 1225, 1155, 1080, 1040, 845 and 760 cm$^{-1}$ (liquid film).

Proton nuclear magnetic resonance spectrum had absorptions at δ=0.97 (t, 3H), 1.8-2.2 (m, 8H), 2.43 (q, 2H), 4.16 (t, 2H), 5.4 (m, 2H) and 6.06 (m, 1H) (in deuterochloroform, TMS internal standard).

EXAMPLE 11

Green Modern Bouquet Note Perfume Composition

|  | % by weight |
|---|---|
| Bergamot oil | 3.0 |
| Lemon oil | 2.0 |
| Ylang-ylang oil (Extra) | 1.0 |
| cis-3-Hexenyl acetate 10% | 0.5 |
| Essence buchu 10% | 0.2 |
| Methylheptenone | 0.3 |
| Benzyl acetate | 2.0 |
| Phenylethyl alcohol | 20.0 |
| Citronellol | 5.0 |
| M.P.C. acetate | 2.5 |
| Hydroxycitronellal | 4.0 |
| Eugenol | 2.0 |
| α-Hexylcinnamylaldehyde | 6.0 |
| Vetivan acetate | 15.0 |
| Oakmoss absolute | 1.0 |
| Peru balsam | 1.0 |
| Galbanum oil | 0.5 |
| Iris-concrete | 1.0 |
| τ-Methylionone | 10.0 |
| Benzyl salicylate | 8.0 |
| Jasmine absolute | 0.5 |
| Amber-Gris 10% (alcohol) | 0.5 |
| Pentalide | 3.0 |
| Dipropylene glycol | 10.0 |
| (Z)-3-Hexenyl angelate | 1.0 |
| Total | 100.0 |

The above-mentioned perfume composition was evaluated by three skilled perfumers as being of higher natural and fresh acceptance and improved fragrant note as compared with a reference composition in which no (Z)-3-hexenyl angelate was incorporated.

EXAMPLE 12

Preparation of 3-Methyl-2-Pentenyl Angelate

A mixture of 22.8 g. of methyl angelate, 10 g. of 3-methyl-2-pentenol, 80 ml. of toluene and 1 g. of dioctyltin acetate was placed in a 300 ml. glass flask, which was equipped with a Soxhlet extractor filled on the top with molecular sieve 4A and a reflux cooler. The above mixture was heated under continuous reflux while returning the refluxed liquid through the molecular sieve 4A to the flask. The mixture resulted from the heating for a total of 17 hours was subjected to single distillation to give 14.2 g. of a distillate boiling at 115° C. (22 mmHg). The distillate was further subjected to rectification to give 9.70 g. of a distillate boiling at 115° C. (22 mmHg). Analysis of the compound by gaschromatography (Column: Silicone SE-52, 2%/chromosorb GHP) indicated a purity of 99.403% in terms of the area ratio. Refractive index (D ray, 20° C.) was 1.463. Infrared spectrum (liquid film) had absorptions at 2850-3020, 1720, 1670, 1650, 1455, 1385, 1350, 1255, 1225, 1155, 1080, 1040, 960, 845 and 760 cm$^{-1}$.

Proton nuclear magnetic resonance spectrum (in deuterochloroform, TMS internal standard) had absorptions at δ=1.01 (t, 3H), 1.72-2.10 (m, 11H), 4.68 (d, 2H), 5.40 (m, 1H) and 6.03 (m, 1H).

EXAMPLE 13

Preparation of 3-Methyl-4-Pentenyl Angelate

A mixture of 22.8 g. of methyl angelate, 10.0 g. of 3-methyl-4-pentenol, 100 ml. of toluene and 0.9 g. of dioctyltin laurate was reacted under the same conditions as in Example 1. The resulting mixture was subjected to single distillation to give 16.91 g. of a distillate boiling at 109° C. (21 mmHg). The distillate was further subjected to rectification to give 12.54 g. of a distillate boiling at 109° C. (21 mmHg). Analysis of the compound by gaschromatography done under the same conditions as in Example 12 indicated a purity of 99.653% in terms of the area ratio. Refractive index was 1.443.

Infrared spectrum had absorptions at 3075, 2850-3000, 1720, 1650, 1455, 1435, 1420, 1390, 1380, 1350, 1260, 1230, 1160, 1080, 1045, 990, 910, 845 and 760 cm$^{-1}$.

Proton nuclear magnetic resonance spectrum (in deuterochloroform, TMS internal standard) had absorptions at δ=1.7-2.04 (m, 9H), 2.41 (t, 2H), 4.29 (t, 2H), 4.91 (m, 2H) and 6.06 (m, 1H).

EXAMPLE 14

A lavender perfume composition for soap was prepared with the following composition:

|  | % by weight |
|---|---|
| Lavender oil Mont Blanc | 50.0 |
| Bergamot oil | 8.0 |
| Bois de rose | 10.0 |
| Geranium oil | 5.0 |
| Rosemary oil | 5.0 |
| Clove oil | 2.5 |
| Patchouli oil | 5.0 |
| Benzoin Siam | 2.5 |
| Coumarin | 4.0 |
| Heliotropin | 5.0 |
| 3-Methyl-2-pentenyl angelate | 3.0 |
| Total | 100.0 |

The above-mentioned composition was evaluated by three skilled perfumers as being of better natural feeling and much improved as compared with a reference composition in which no 3-methyl-2-pentenyl angelate was incorporated.

EXAMPLE 15

Jasmine Compound

|  | % by weight |
|---|---|
| α-Hexylcinnamaldehyde | 75.0 |
| Benzoin siam | 1.0 |
| Jasmine absolute | 5.0 |
| Benzyl benzoate | 3.0 |
| Benzyl acetate | 8.0 |
| Linalol | 2.5 |
| Civet absolute 10% (alcohol) | 0.5 |
| Indol 10% | 3.0 |
| cis-Jasmone | 0.5 |
| τ-Lactone C-11 | 0.5 |
| 3-Methyl-4-pentenyl angelate | 1.0 |
| Total | 100.0 |

The above-mentioned perfume composition was evaluated by three skilled perfumers as being of better natural feeling and much improved note as compared with a reference composition in which no 3-methyl-4-pentenyl angelate was incorporated.

EXAMPLE 16

Preparation of Amyl Angelate

A mixture of 80.0 g. of methyl angelate, 65.0 g. of amyl alcohol, 200 ml. of toluene and 4.0 g. of dioctyltin laurate was placed in a 500 ml. glass flask, which was equipped with a Soxhlet extractor filled on the top with molecular sieve 4A and a reflux cooler. The above mixture was heated under continued reflux while returning the refluxed liquid through the molecular sieve 4A to the flask.

The mixture resulted from the heating for a total of 24 hours was subjected to single distillation to give 98.3 g. of a distillate boiling at 85°–100° C. (30 mmHg).

The distillate was further subjected to rectification to give 64.8 g. of a distillate boiling at 94° C. (30 mmHg). Analysis of the compound by gas-chromatography (Capillary column: 25 m×0.3 mm$\phi$ PEG 20M) indicated a purity of 99.8% in terms of the area ratio.

Refractive index (D ray, 20° C.) was 1.4375. Infrared spectrum had absorptions at 2860–3020, 1720, 1650, 1455, 1390, 1380, 1350, 1260, 1230, 1160, 1085, 1045, 975, 845, 760 and 730 cm$^{-1}$ (liquid film).

Proton nuclear magnetic resonance spectrum had absorptions at $\delta=0.91$ (t, 3H), 1.28–1.79 (m, 6H), 1.85–2.04 (m, 6H), 4.14 (t, 2H) and 6.03 (m, 1H).

Carbon-13 nuclear magnetic resonance spectrum had absorptions at $\delta=13.98, 15.68, 20.61, 22.51, 28.50, 28.66, 64.20, 128.45, 137.17$ and $168.00$ Organic elementary analysis indicated C=70.31%, H=10.39%.

EXAMPLES 17-22

Esters of angelic acid with other alcohols were prepared in the same way as in Example 16. Physical properties and analytical values were shown in Table 1.

TABLE 1-1

| Example | Angelate (structural formula, molecular formula) | Characteristics | Boiling Point | Refraction Index ($n_D$ 20) | IR (cm$^{-1}$) | NMR (ppm) (in CDCl$_3$, TMS Standard) H$^1$ | NMR (ppm) (in CDCl$_3$, TMS Standard) C$^{13}$ | MS (M$^+$) | Elementary Analysis C (%) | Elementary Analysis H (%) |
|---|---|---|---|---|---|---|---|---|---|---|
| 17 | 2-methylpropenyl angelate (C$_9$H$_{14}$O$_2$) | Colorless liquid | 90° C./ 32 mmHg | 1.4527 | 3070, 2885–3050, 1720, 1660, 1450, 1380, 1350, 1260, 1230, 1150, 1090, 1040, 990, 960, 900, 850, 760 | 1.80 (m, 3H) 1.9–2.1 (m) 4.59 (s, 2H) 4.96 (d, 2H) 6.10 (m, 1H) | 15.74, 19.58 20.59, 67.42 112.74 128.12 137.93 140.37 167.48 | 154 | 70.06 | 9.23 |
| 18 | 2-methylbutyl angelate (C$_{10}$H$_{18}$O$_2$) | Colorless liquid | 98° C./ 26 mmHg | 1.4391 | 2850–3050, 1720, 1650, 1460, 1390, 1350, 1260, 1230, 1160, 1090, 1040, 990, 850, 760 | 0.93 (d, 3H) 0.8–2.10 (m, 12H) 4.02 (m, 2H) 6.04 (m, 1H) | 11.30, 15.71 16.69, 20.64 26.44, 34.51 68.77 128.45 137.28 167.97 | 170 | 70.34 | 10.44 |
| 19 | benzyl angelate (C$_{12}$H$_{14}$O$_2$) | Colorless liquid | 92° C./ 2 mmHg | 1.5148 | 2850–3120, 2725, 1960, 1880, 1800, 1720, 1650, 1605, 1585, 1500, 1450, 1385, 1350, 1255, 1230, 1140, 965, 800, 760, 730, 700, 675 | 1.89–2.02 (m, 6H) 5.18 (s, 2H) 6.02 (m, 1H) 7.20–7.40 (m, 5H) | 15.72, 20.53 65.80, 127.99 128.50 136.50 137.96 167.65 | 190 | 75.68 | 7.33 |

TABLE 1

| Example | Angelate (structural formula, molecular formula) | Characteristics | Boiling Point | Refraction Index | IR (cm$^{-1}$) | NMR (ppm) (in CDCl$_3$, TMS Standard) H$^1$ | NMR (ppm) (in CDCl$_3$, TMS Standard) C$^{13}$ | MS (M$^+$) | Elementary Analysis C (%) | Elementary Analysis H (%) |
|---|---|---|---|---|---|---|---|---|---|---|
| 20 | β-phenylethyl angelate (C$_{13}$H$_{16}$O$_2$) | Colorless liquid | 84° C./ 0.5 mmHg | 1.5103 | 2860–3090, 1720, 1655, 1605, 1500, 1455, 1390, 1355, 1260, 1235, 1160, 1085, 1045, 995, 850, 755, 700, | 1.82–1.96 (m, 6H) 2.95(t, 2H) 4.34(t, 2H) 5.90(m, 1H) 7.17–7.39 (m, 5H) | 15.66, 20.53 35.32, 64.58 126.52, 128.04 128.47, 128.76 137.68 138.17 167.51 | 204 | 76.29 | 7.77 |

TABLE 1-continued

| Example | Angelate (structural formula, molecular formula) | Characteristics | Boiling Point | Refraction Index | IR (cm$^{-1}$) | NMR (ppm) (in CDCl$_3$, TMS Standard) H$^1$ | NMR C$^{13}$ | MS (M+) | Elementary Analysis C (%) | H (%) |
|---|---|---|---|---|---|---|---|---|---|---|
| 21 | gelanyl angelate (C$_{15}$H$_{24}$O$_2$) | Colorless liquid | 102° C./ 1.2 mmHg | 1.4773 | 2860–3020, 1720, 1655, 1450, 1385, 1355, 1255, 1230, 1155, 1085, 1040, 960, 850, 760 | 1.69–2.06 (m, 19H), 4.66(d, 2H), 5.08(m, 1H), 5.40(t, 1H), 6.01(m, 1H) | 15.68, 16.44, 17.66, 20.64, 25.65, 26.52, 39.68, 60.89, 119.24, 124.03, 128.42, 131.56, 137.09, 141.61, 167.81 | 236 | 76.03 | 10.01 |
| 22 | citronellyl angelate (C$_{15}$H$_{26}$O$_2$) | Colorless liquid | 105° C./ 0.5 mmHg | 1.4616 | 2850–3020, 1720, 1655, 1460, 1385, 1355, 1260, 1230, 1060, 1085, 1045, 980, 850, 760 | 0.93(d, 2H), 1.11–2.12 (m, 19H), 4.19(t, 1H), 5.09(m, 1H), 6.02(m, 1H) | 15.65, 17.63, 19.53, 20.55, 25.52, 25.65, 29.74, 35.76, 37.13, 62.58, 124.72, 128.35, 131.23, 137.06, 168.09 | 238 | 75.51 | 10.81 |

EXAMPLE 23

An example of the formulations in which 2-methylpropenyl angelate was used: Rosy type

| | % by weight |
|---|---|
| Phenylethyl alcohol | 50.0 |
| Rhodinol pure | 20.0 |
| Geranium oil | 6.0 |
| Geranyl acetate | 4.0 |
| Nerol | 3.0 |
| Trichloromethylphenylcarbinyl acetate | 2.5 |
| Phenylethyl acetate | 2.5 |
| Hydroxycitronellal | 2.0 |
| Methyleugenol | 2.0 |
| Undecylaldehyde 10% (in triethyl citrate) | 2.0 |
| Palmarosa oil | 2.0 |
| Guaiacyl acetate | 1.5 |
| Citral | 1.0 |
| Dimethylbenzylcarbinyl acetate | 1.0 |
| 2-Methylpropenyl angelate | 0.5 |
| Total | 100.0 |

The above-mentioned perfume composition was evaluated as being of increased natural, diffusible and green floral feeling.

EXAMPLE 24

An example of the formulations using n-amyl angelate: Fragrant olive type

| | % by weight |
|---|---|
| Ethyl caprate | 1.0 |
| Linalool | 10.0 |
| Benzyl acetate | 10.0 |
| Methyl ionone | 5.0 |
| Ethyl butyrate | 0.5 |
| Amyl acetate | 1.0 |
| Benzaldehyde | 0.3 |
| Phenylethyl acetate | 3.0 |
| Geranyl acetate | 1.0 |
| Anethole | 1.0 |
| β-Pinene | 10.0 |
| τn-Decalactone | 6.0 |
| Benzyl propionate | 5.0 |
| Phenylethyl alcohol | 10.0 |
| Amylcinnamaldehyde | 5.0 |
| Dihydromyrcenol | 0.5 |
| Phenylethyl isobutyrate | 10.0 |
| Geraniol | 5.0 |
| Linalyl acetate | 5.0 |
| Hydroxycitronellal | 5.0 |
| Indole | 0.2 |
| Ethyl caproate | 0.5 |
| n-Amyl angelate | 5.0 |
| Total | 100.0 |

The above-mentioned perfume composition had emphasized lactone sweetness and improved floral feeling as compared with a reference composition with no n-amyl angelate incorporated.

EXAMPLE 25

An example of the formulations using 2-methylbutyl angelate: Floral bouquet type

| | % by weight |
|---|---|
| Hexylcinnamaldehyde | 25.0 |
| Hydroxycitronellal | 15.0 |
| Rhodinol | 10.0 |
| Tetrahydrolinalol | 7.0 |
| Benzyl salicylate | 6.0 |
| Indole 10% (in triethyl citrate) | 5.0 |
| Hexyl salicylate | 5.0 |
| Lily aldehyde | 5.0 |
| Benzyl acetate | 5.0 |
| Linalol | 3.0 |
| Ylang-ylang oil extra | 2.5 |
| Sandeol | 2.5 |
| Cinnamic alcohol | 1.5 |
| Geranium oil | 1.5 |
| 2-Methylbutyl angelate | 5.0 |
| Total | 100.0 |

The above-mentioned perfume composition had improved natural and elegant floral feeling as compared with a reference composition with no 2-methylbutyl angelate.

EXAMPLE 26

An example of the formulations using benzyl angelate: Tulip type

| | % by weight |
|---|---|
| Benzylphenyl acetate | 30.0 |
| Coumarin | 5.0 |
| Dimethylhydroquinone | 3.0 |
| Geraniol | 6.0 |

-continued

| | % by weight |
|---|---|
| Nerol | 3.0 |
| Citronellol | 8.0 |
| Phenylethyl alcohol | 10.0 |
| Phenylethyl acetate | 5.0 |
| Ionone pure | 5.0 |
| Guaiac wood oil | 10.0 |
| Geranium oil | 1.0 |
| Benzaldehyde | 1.0 |
| Aldehyde $C_{14}$ 100% | 1.0 |
| Benzyl angelate | 7.0 |
| Total | 100.0 |

The above-mentioned perfume composition had improved fresh floral and natural feeling as compared with a reference composition with no benzyl angelate incorporated.

EXAMPLE 27

An example of the formulations using β-phenylethyl angelate: Rosy type

| | % by weight |
|---|---|
| Geraniol | 15.0 |
| Citronellol | 20.0 |
| Phenylethyl alcohol | 50.0 |
| Geranyl acetate | 3.0 |
| Geranyl butyrate | 1.0 |
| Guaiac wood oil | 6.0 |
| Aldehyde C-11 | 0.5 |
| Phenylacetic acid 10% | 0.5 |
| Geranium bourbon oil | 3.5 |
| β-Phenylethyl angelate | 0.5 |
| Total | 100.0 |

The above-mentioned perfume composition had improved fresh and natural feeling as compared with a reference composition with no β-phenylethyl angelate incorporated.

EXAMPLE 28

An example of the formulations using geranyl angelate: Rosy type

| | % by weight |
|---|---|
| Phenylethyl alcohol | 47.0 |
| Geraniol | 12.0 |
| Citronellol | 18.0 |
| Geranium S.B.S. | 1.5 |
| Phenylethyl formate | 0.5 |
| Nerol | 6.5 |
| Phenylethyl acetate | 3.5 |
| Nerolidol | 1.5 |
| Phenylethyl phenylacetate | 5.5 |
| Phenylethyl salicylate | 0.5 |
| Rose phenone | 3.5 |
| Geranyl angelate | 1.0 |
| Total | 100.0 |

The above-mentioned perfume composition provided more sweetness of Bulgarian rose and fresh pleasant blue note and improved rosy fragrance as compared with a reference composition with no geranyl angelate incorporated.

EXAMPLE 29

An example of the formulations using citronellyl angelate: Fusea for soap

| | % by weight |
|---|---|
| Lavender oil | 20.0 |
| Bergamot oil (Synthetic) | 15.0 |
| Geranium oil | 10.0 |
| p-tert-Butylcyclohexyl acetate | 10.0 |
| Terpeneol | 7.5 |
| Coumarin | 7.0 |
| Tetrahydrolinallol | 5.0 |
| Amyl salicylate | 5.0 |
| Lily aldehyde pure | 5.0 |
| Linalyl acetate | 5.0 |
| Sandeol | 4.0 |
| Absolute tree moss | 1.5 |
| Citronellyl angelate | 5.0 |
| Total | 100.0 |

The above-mentioned perfume composition had improved natural mild rosy note as compared with a reference composition with no citronellyl angelate incorporated.

EXAMPLE 30

Preparation of Heptyl Angelate

A mixture of 50.0 g. of methyl angelate, 53.4 g. of heptyl alcohol, 200 ml. of toluene and 2.5 g. of dioctyltin laurate was placed in a 500 ml. glass flask, which was equipped with a Soxhlet extractor filled on the top with molecular sieve 4A and a reflux cooler. The mixture was heated under continuous reflux while returning the refluxed liquid through the molecular sieve 4A to the flask. The mixture resulted from the heating for a total of 16 hours was subjected to single distillation to give 74.54 g. of a distillate boiling at 75°–89° C. (2 mmHg).

The distillate was further subjected to rectification to give 63.98 g. of a distillate boiling at 82° C. (5 mmHg). Analysis of the compound by gas-chromatography (Capillary column: 25 m×0.3 mmφ PEG 20M) indicated a purity of 99.3% in terms of the area ratio.

Refractive index (D ray, 20° C.) was 1.4420. Infrared spectrum had absorptions at 2860–3020, 1720, 1650, 1455, 1390, 1380, 1355, 1260, 1230, 1160, 1085, 1045, 850, 760 and 730 cm$^{-1}$ (liquid film).

Proton nuclear magnetic resonance spectrum (deuterochloroform, TMS internal standard) had absorptions at δ=0.89 (t, 3H), 1.08–1.81 (m, 10H), 1.86–2.04 (m, 6H), 4.14 (t, 2H) and 6.02 (m, 1H) ppm.

Carbon-13 nuclear magnetic resonance spectrum (deuterochloroform, TMS internal standard) had absorptions at δ=14.07, 15.68, 20.60, 22.72, 26.26, 28.96, 29.11, 31.91, 64.24, 75.91, 77.33, 128.43, 137.06 and 168.02 ppm.

Organic elementary analysis indicated C=72.52% and H=11.12%.

EXAMPLES 31–40

Esters of angelic acid with other alcohols were prepared in the same way as in Example 30. Physical properties and analytical values were shown in Table 2.

TABLE 2

| Example | Angelate (structural formula, molecular formula) | Characteristics | Boiling Point | Refraction Index ($n_D^{20}$) | IR (cm$^{-1}$) |
|---|---|---|---|---|---|
| 31 | n-hexyl angelate 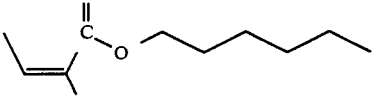 (C$_{11}$H$_{20}$O$_2$) | Colorless liquid | 93° C./ 7 mmHg | 1.4400 | 2860–3020, 1720, 1650, 1460, 1390, 1260, 1230, 1160, 1090, 1040, 990, 850, 760, 730 |
| 32 | n-octyl angelate 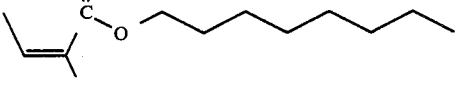 (C$_{13}$H$_{24}$O$_2$) | Colorless liquid | 70° C./ 0.06 mmHg | 1.4442 | 2860–3020, 1720, 1650, 1460, 1390, 1380, 1355, 1260, 1230, 1160, 1085, 1045, 850, 760, 730 |
| 33 | n-nonyl angelate 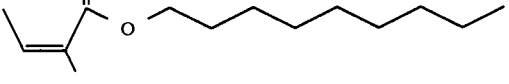 (C$_{14}$H$_{26}$O$_2$) | Colorless liquid | 90° C./ 0.05 mmHg | 1.4461 | 2860–3020, 1720, 1650, 1460, 1390, 1380, 1355, 1260, 1230, 1160, 1085, 1045, 970, 850, 760, 720 |
| 34 | n-decyl angelate 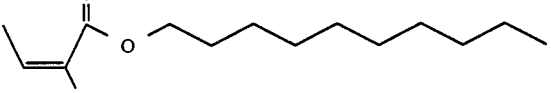 (C$_{15}$H$_{28}$O$_2$) | Colorless liquid | 95° C./ 0.05 mmHg | 1.4480 | 2860–3020, 1720, 1655, 1460, 1390, 1380, 1355, 1260, 1230, 1160, 1085, 1045, 980, 850, 760, 720 |
| 35 | cyclopentyl angelate 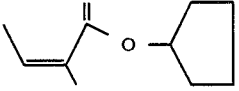 (C$_{10}$H$_{16}$O$_2$) | Colorless liquid | 100° C./ 90 mmHg | 1.4601 | 2860–3040, 1720, 1650, 1455, 1435, 1385, 1365, 1350, 1320, 1260, 1230, 1085, 1040, 965, 900, 850, 760 |
| 36 | cyclohexyl angelate 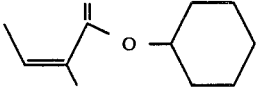 (C$_{11}$H$_{18}$O$_2$) | Colorless liquid | 106° C./ 100 mmHg | 1.4650 | 2855–3020, 1720, 1650, 1450, 1390, 1355, 1330, 1315, 1255, 1230, 1190, 1165, 1150, 1100, 1085, 1040, 1020, 960, 925, 915, 890, 845, 760 |
| 37 | 2-methylpentyl angelate 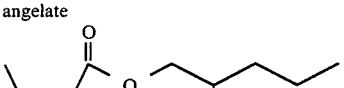 (C$_{11}$H$_{20}$O$_2$) | Colorless liquid | 95° C./ 115 mmHg | 1.4399 | 2870–3020, 1720, 1650, 1455, 1390, 1380, 1350, 1260, 1230, 1160, 1085, 1045, 975, 845, 760, 740 |

TABLE 2-continued
| 38 | α-methylbenzyl angelate 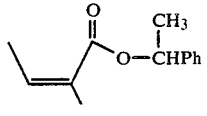 ($C_{13}H_{16}O_2$) | | Colorless liquid | 79° C./ 0.07 mmHg | 1.5066 | 2860–3090, 1960, 1880, 1720, 1655, 1605, 1590, 1500, 1455, 1390, 1360, 1330, 1305, 1285, 1260, 1230, 1210, 1160, 1095, 1065, 1400, 1030, 1010, 1000, 945, 910, 850, 765, 700 |
|---|---|---|---|---|---|---|
| 39 | neryl angelate 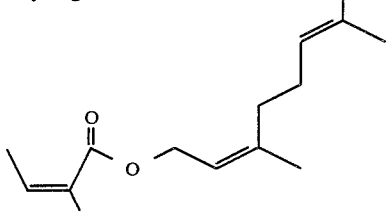 ($C_{15}H_{24}O_2$) | | Colorless liquid | 86° C./ 0.1 mmHg | 1.4768 | 2850–3020, 2725, 1720, 1650, 1450, 1380, 1355, 1255, 1230, 1155, 1085, 1040, 965, 845, 760, 740 |
| 40 | furfuryl angelate 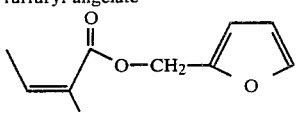 ($C_{10}H_{12}O_3$) | | pale yellow liquid | 136° C./ 49 mmHg | 1.4846 | 2950–3100, 3140, 1720, 1650, 1605, 1500, 1450, 1430, 1380, 1250, 1220, 1160, 1090, 1040, 1010, 960, 920, 890, 850, 810, 740 |
| Example | NMR (in $CDCl_3$, TMS Standard) | | MS ($M^+$) | Elementary Analysis | |
|---|---|---|---|---|---|
| | $H^1$ (ppm) | $C^{13}$ (ppm) | | C (%) | H (%) |
| 31 | 0.90 (t, 3H) 1.1–2.1 (m, 14H) 4.16 (t, 2H) 6.05 (q, 1H) | 14.03, 15.68 20.61, 22.78 26.03, 28.93 31.72, 64.17 128.45, 137.20 167.81 | 184 | 71.65 | 10.73 |
| 32 | 0.88 (t, 3H) 1.08–1.81 (m, 12H) 1.87–2.04 (m, 6H) 4.14 (t, 2H) 6.02 (m, 1H) | 14.14, 15.71 20.64, 22.86 26.36, 29.01 29.47, 32.04 64.17, 128.45 137.20, 167.83 | 212 | 73.62 | 11.51 |
| 33 | 0.88 (t, 3H) 1.08–1.81 (m, 14H) 1.87–2.04 (m, 6H) 4.14 (t, 2H) 6.02 (m, 1H) | 14.11, 15.68 20.61, 22.89 26.36, 29.01 29.50, 29.77 32.12, 64.11 128.45, 137.14 167.70 | 226 | 74.13 | 11.63 |
| 34 | 0.88 (t, 3H) 1.14–1.78 (m, 16H) 1.87–2.04 (m, 6H) 4.14 (t, 2H) 6.03 (m, 1H) | 14.11, 15.68 20.59, 22.81 26.27, 28.93 29.44, 29.69 32.07, 64.20 128.37, 137.14 167.94 | 240 | 74.81 | 11.35 |
| 35 | 1.69–2.00 (m, 14H) 5.23 (m, 1H) 6.02 (m, 1H) | 15.63, 20.61 23.95, 32.99 76.77, 128.75 136.63 167.72 | 168 | 71.33 | 9.46 |
| 36 | 1.36–2.04 (m, 16H) 4.85 (m, 1H) 6.01 (m, 1H) | 15.68, 20.64 23.84, 25.73 31.85, 72.11 128.83 136.60 | 182 | 72.35 | 9.88 |

TABLE 2-continued

| | | | | | |
|---|---|---|---|---|---|
| | | 167.40 | | | |
| 37 | 0.84–1.00 (m, 6H) | 14.30, 15.71 | 184 | 71.88 | 10.63 |
| | 1.12–1.46 (m, 6H) | 17.17, 20.18 | | | |
| | 3.98 (m, 2H) | 20.64, 32.64 | | | |
| | 6.02 (m, 1H) | 36.05, 69.07 | | | |
| | | 128.45, 137.28 | | | |
| | | 167.89 | | | |
| 38 | 1.54 (d, 3H) | 15.70, 20.57 | 204 | 76.33 | 7.65 |
| | 1.88–2.01 (m, 6H) | 22.50, 72.04 | | | |
| | 5.85–6.15 (m, 2H) | 126.09, 127.72 | | | |
| | 7.28–7.42 (m, 5H) | 128.30, 128.50 | | | |
| | | 137.42, 142.18 | | | |
| | | 167.07 | | | |
| 39 | 1.60–2.14 (m, 19H) | 15.79, 17.72 | 236 | 76.01 | 10.18 |
| | 4.63 (t, 2H) | 20.72, 23.56 | | | |
| | 4.95–5.23 (m, 1H) | 25.73, 26.92 | | | |
| | 5.40 (t, 1H) | 32.45, 60.70 | | | |
| | 6.01 (m, 1H) | 120.10, 123.98 | | | |
| | | 128.45, 132.02 | | | |
| | | 137.28, 141.91 | | | |
| | | 167.86 | | | |
| 40 | 1.8–2.1 (m, 6H) | 15.68, 20.45 | 164 | 73.06 | 7.14 |
| | 5.14 (s, 2H) | 57.70, 110.38 | | | |
| | 6.07 (q, 1H) | 110.62, 127.88 | | | |
| | 4.3–4.5 (m, 2H) | 138.25 | | | |
| | 5.40 (d, 1H) | 143.16 | | | |
| | | 150.25 | | | |
| | | 167.32 | | | |

EXAMPLE 41

An example of the formulations using n-hexyl angelate: Gardenia type

| | % by weight |
|---|---|
| Heliotropin | 5.0 |
| Pentalide | 2.0 |
| Methylphenylcarbinyl acetate | 3.0 |
| cis-3-Hexenol | 1.0 |
| cis-3-Hexenyl benzoate | 3.0 |
| Ylang-ylang oil | 3.0 |
| Linalol | 15.0 |
| Linalyl acetate | 5.0 |
| Gammanonyl lactone | 2.0 |
| Hydroxycitronellal | 20.0 |
| Jasmine compound | 8.0 |
| Alpha-ionone | 10.0 |
| Cinnamic alcohol | 4.0 |
| Phenylethyl alcohol | 10.0 |
| Dimethylbenzylcarbinol | 4.0 |
| n-Hexyl angelate | 5.0 |
| Total | 100.0 |

The above-mentioned perfume composition had better natural floral and fresh feeling as compared with a reference composition with no n-hexyl angelate incorporated.

EXAMPLE 42

An example of the formulations using n-heptyl angelate: Rose muget type

| | % by weight |
|---|---|
| Linalool | 2.5 |
| Benzyl acetate | 1.5 |
| Rhodinol | 5.0 |
| Lily aldehyde | 10.0 |
| Ethylene brassylate | 5.0 |
| Hyacinth oil | 0.5 |
| Geranium oil | 1.5 |
| Geraniol | 8.0 |
| Phenylethyl alcohol | 10.0 |
| Hydroxycitranollal | 30.0 |
| Hexylcinnamaldehyde | 20.0 |

-continued

| | % by weight |
|---|---|
| Phenylpropyl alcohol | 0.3 |
| Indole | 0.2 |
| Petitgrain | 0.5 |
| n-Heptyl angelate | 5.0 |
| Total | 100.0 |

The above-mentioned perfume composition had emphasized floral feeling by increasing rose fragrance as compared with a reference composition with no n-heptyl angelate incorporated.

EXAMPLE 43

An example of the formulations using n-octyl angelate: Hyacinth type

| | % by weight |
|---|---|
| Artificial hyacinth, MS | 80.0 |
| Styrax resin | 1.5 |
| Indole 10% | 1.0 |
| Ylang-ylang essential oil | 1.0 |
| 5-Cyclohexadecinone | 0.5 |
| Jasmine absolute | 0.1 |
| cis-3-Hexenyl salicylate | 1.4 |
| Phenylethyl alcohol | 10.0 |
| n-Octyl angelate | 4.0 |
| Total | 100.0 |

The above-mentioned perfume composition had improved brilliant, light, floral feeling by increasing fragrance of phenylethyl alcohol as compared with a reference composition with no n-octyl angelate incorporated.

EXAMPLE 44

An example of the formulations using n-nonyl angelate: Rosy type

| | % by weight |
|---|---|
| Bulgarian rose oil | 1.0 |

-continued

| | % by weight |
|---|---|
| Rose absolute | 2.0 |
| Phenylethyl alcohol | 30.0 |
| Phenylethyl acetate | 7.5 |
| Linalool | 6.0 |
| Benzyl acetate | 7.5 |
| Bergamot oil | 5.0 |
| l-Citronellol | 18.5 |
| Geraniol | 20.0 |
| n-Nonyl angelate | 2.5 |
| Total | 100.0 |

The above-mentioned perfume composition had increased green-note freshness and retainability as compared with a reference composition with no n-nonyl angelate incorporated.

EXAMPLE 45

An example of the formulations using n-decyl angelate: Lilac type

| | % by weight |
|---|---|
| Cinnamyl alcohol | 32.0 |
| Terpineol | 32.0 |
| Hydroxycitronellol | 10.0 |
| Benzyl acetate | 7.0 |
| Ylang-ylang oil | 6.0 |
| Phenylethyl alcohol | 11.0 |
| n-Decyl angelate | 2.0 |
| Total | 100.0 |

The above-mentioned perfume composition had increased white image of lilac and floral feeling and added natural feeling being more lilac-like as compared with a reference composition with no n-decyl angelate incorporated.

EXAMPLE 46

An example of the formulations using cyclopentyl angelate: Cologne type for shampoo

| | % by weight |
|---|---|
| Petigrain oil | 25.0 |
| Artificial lemon oil | 20.0 |
| Lavandine oil | 20.0 |
| Sweet orange oil | 4.0 |
| Methylphenylcarbinyl acetate | 1.0 |
| Cinnamic alcohol | 2.0 |
| Citronellol | 5.0 |
| Dihydroterpinyl acetate | 5.0 |
| α-Amylcinnamaldehyde | 5.0 |
| Patchouli Singapore | 2.0 |
| Lavandine oil | 0.5 |
| Benzoin resin | 1.0 |
| Ethylene brassylate | 3.0 |
| 5-Cyclohexadecenone | 1.0 |
| Coumarin | 5.0 |
| Thyme oil | 0.2 |
| Aldehyde C-10 | 0.2 |
| Aldehyde C-11 | 0.1 |
| Cyclopentyl angelate | 1.0 |
| Total | 100.0 |

The above-mentioned perfume composition had increased strength and diffusibility and emphasized rose-like soft note as compared with a reference composition with no cyclopentyl angelate incorporated.

EXAMPLE 47

An example of the formulations using cyclohexyl angelate: Herbal type for room fresh corner

| | % by weight |
|---|---|
| Amylcinnamaldehyde | 20.0 |
| Cedar wood oil | 20.0 |
| Phenylethyl alcohol | 15.0 |
| Amyl salicylate | 10.0 |
| Pine needle oil | 5.0 |
| Lavandine oil | 5.0 |
| Petitgrain oil (Paraguay) | 5.0 |
| Lily aldehyde | 5.0 |
| cis-3-Hexenol | 2.5 |
| Spearmint oil 10% (in triethyl citrate) | 2.0 |
| Lavandine absolute | 1.5 |
| Sandeol | 1.0 |
| Cedar leef oil | 0.5 |
| cis-3-Hexenyl acetate | 0.5 |
| Methyldihydrojasmonate | 0.5 |
| Cyclohexyl angelate | 1.0 |
| Total | 100.0 |

The above-mentioned perfume composition had emphasized fresh, soft, floral green note as compared with a reference composition with no cyclohexyl angelate incorporated.

EXAMPLE 48

An example of the compositions using 2-methylpentyl angelate: Geranium type-artificial

| | % by weight |
|---|---|
| Geraniol | 30.0 |
| l-Citronellol | 35.0 |
| Citronellyl formate | 9.0 |
| Geranyl formate | 5.0 |
| Geranyl acetate | 5.0 |
| Linalool | 10.0 |
| Rose oxide (10% α-pinene) | 3.0 |
| Dimethyl sulfide (10% α-pinene) | 0.5 |
| l-Menthone | 2.0 |
| 2-Methylpentyl angelate | 0.5 |
| Total | 100.0 |

The above-mentioned perfume composition had increased strength and diffusibility of artificial geranium oil with higher natural feeling.

EXAMPLE 49

An example of the composition using α-methylbenzyl angelate: Orchid type

| | % by weight |
|---|---|
| Amyl salicylate | 11.0 |
| Isobutyl salicylate | 12.0 |
| Linalool | 7.0 |
| Hydroxycitronellal | 5.0 |
| Ylang-ylang oil | 8.0 |
| Heliotropin | 3.0 |
| Coumarin | 1.0 |
| Pentalide | 5.0 |
| 5-Cyclohexadecenone | 2.0 |
| Oak moss absolute | 0.3 |
| Vanillin | 0.7 |
| Phenylacetaldehyde | 2.0 |
| Phenylethyl alcohol | 10.0 |
| Benzyl acetate | 4.0 |
| Neroli oil | 3.0 |
| Anisaldehyde | 2.0 |
| Methylionone | 10.0 |

|  | % by weight |
|---|---|
| α-Methylbenzyl angelate | 15.0 |
| Total | 100.0 |

The above-mentioned perfume composition had increased floral feeling as compared with a reference composition with no α-methylbenzyl angelate incorporated.

EXAMPLE 50

An example of the formulations using neryl angelate: Fancy rose type

|  | % by weight |
|---|---|
| Rose P | 20.0 |
| Geraniol | 5.0 |
| Citronellol | 10.0 |
| Nerol | 3.0 |
| Hydroxycitronellal | 2.0 |
| Rhodinol | 28.0 |
| Rose essence | 1.0 |
| Guaiac wood oil | 5.0 |
| Rosephenone | 1.0 |
| Benzyl alcohol | 2.0 |
| Benzyl acetate | 3.5 |
| Linalool | 3.0 |
| Geranium Bourbon | 1.0 |
| Methylphenylcarbinyl acetate | 0.5 |
| Heliotropin | 1.0 |
| Coumarin | 2.0 |
| Pentalide | 1.0 |
| β-Ionone | 5.0 |
| Benzyl salicylate | 4.0 |
| Neryl angelate | 2.0 |
| Total | 100.0 |

The above-mentioned perfume composition had increased body and sweetness and more floral fragrance as compared with a reference composition with no neryl angelate incorporated.

EXAMPLE 51

An example of the formulations using furfuryl angelate: Opoponax type

|  | % by weight |
|---|---|
| Bergamot oil | 30.0 |
| Clove vanillin | 5.0 |
| Coumarin | 8.0 |
| Santalol | 8.0 |
| Vetiverol | 6.0 |
| Musk ketone | 3.5 |
| Myrrh resinoid | 5.0 |
| Castorium absolute | 0.5 |
| Benzoin resinoid | 5.0 |
| Tall resinoid | 4.0 |
| α-Ionone | 3.0 |
| Linalyl acetate | 4.0 |
| Olibanum resinoid | 3.5 |
| Furfuryl angelate | 5.0 |
| Total | 100.0 |

The above-mentioned perfume composition had better light and fresh feeling as compared with a reference composition with no furfuryl angelate incorporated.

EXAMPLE 52

Preparation of heptyl angelate

A mixture of 50.0 g. of methyl angelate, 53.4 g. of heptyl alcohol, 200 ml. of toluene and 2.5 g. of dioctyltin laurate was placed in a glass flask, which was equipped with a Soxhlet extractor filled on the top with molecular sieve 4A and a reflux coller. The above mixture was heated under continuous reflux while returning the refluxed liquid through the molecular sieve 4A to the flask. The mixture resulted from the heating for a total of 16 hours was subjected to single distillation to give 74.54 g. of a distillate boiling at 75°–89° C. (2 mmHg).

The distillate was further subjected to rectification to give 63.98 g. of a distillate boiling at 82° C. (5 mmHg). Analysis of the compound by gas-chromatography (Capillary column: 25 m×0.3 mmφ PEG 20M) indicated a purity of 99.3% in terms of the area ratio.

Refractive index (D ray, 20° C.) was 1.4420. Infrared spectrum had absorptions at 2860–3020, 1720, 1650, 1455, 1390, 1380, 1355, 1260, 1230, 1160, 1085, 1045, 850, 760 and 730 cm$^{-1}$ (liquid film).

Proton nuclear magnetic resonance spectrum (deuterochloroform, TMS internal standard) had absorptions at δ=0.89 (t, 3H), 1.08–1.81 (m, 10H), 1.86–2.04 (m, 6H), 4.14 (t, 2H) and 6.02 (m, 1H) ppm.

Carbon-13 nuclear magnetic resonance spectrum (deuterochloroform, TMS internal standard) had absorptions at δ=14.07, 15.68, 20.60, 22.72, 26.26, 28.96, 29.11, 31.91, 64.24, 75.91, 77.33, 128.43, 137.06 and 168.02 ppm.

Organic elementary analysis indicated C=72.52%, H=11.12%.

EXAMPLES 53–62

Esters of angelic acid with other alcohols were prepared in the same way as in Example 52. Physical properties and analytical values were shown in Table 3.

TABLE 3

| Example | Angelate structural formula, molecular formula | Characteristics | Boiling Point | Refraction Index ($n_D^{20}$) | IR (cm$^{-1}$) |
|---|---|---|---|---|---|
| 53 | n-hexyl angelate ($C_{11}H_{20}O_2$) | Colorless liquid | 93° C./ 7 mmHg | 1.4400 | 2860–3020, 1720, 1650, 1460, 1390, 1260, 1230, 1160, 1090, 1040, 990, 850, 760, 730 |

TABLE 3-continued

| | | | | | |
|---|---|---|---|---|---|
| 54 | n-octyl angelate (C₁₃H₂₄O₂) | Colorless liquid | 70° C./ 0.06 mmHg | 1.4442 | 2860–3020, 1720, 1650, 1460, 1390, 1380, 1355, 1260, 1230, 1160, 1085, 1045, 850, 760, 730 |
| 55 | n-nonyl angelate (C₁₄H₂₆O₂) | Colorless liquid | 90° C./ 0.05 mmHg | 1.4461 | 2860–3020, 1720, 1650, 1460, 1390, 1380, 1355, 1260, 1230, 1160, 1085, 1045, 970, 850, 760, 720 |
| 56 | n-decyl angelate (C₁₅H₂₈O₂) | Colorless liquid | 95° C./ 0.05 mmHg | 1.4480 | 2860–3020, 1720, 1655, 1460, 1390, 1380, 1355, 1260, 1230, 1160, 1085, 1045, 980, 850, 760, 720 |
| 57 | cyclopentyl angelate (C₁₀H₁₆O₂) | Colorless liquid | 100° C./ 90 mmHg | 1.4601 | 2860–3040, 1720, 1650, 1455, 1435, 1385, 1365, 1350, 1320, 1260, 1230, 1085, 1040, 965, 900, 850, 760 |
| 58 | cyclohexyl angelate (C₁₁H₁₈O₂) | Colorless liquid | 106° C./ 100 mmHg | 1.4650 | 2855–3020, 1720, 1650, 1450, 1390, 1355, 1330, 1315, 1255, 1230, 1190, 1165, 1150, 1100, 1085, 1040, 1020, 960, 925, 915, 890, 845, 760 |
| 59 | 2-methylpentyl angelate (C₁₁H₂₀O₂) | Colorless liquid | 95° C./ 115 mmHg | 1.4399 | 2870–3020, 1720, 1650, 1455, 1390, 1380, 1350, 1260, 1230, 1160, 1085, 1045, 975, 845, 760, 740 |
| 60 | α-methylbenzyl angelate (C₁₃H₁₆O₂) | Colorless liquid | 79° C./ 0.07 mmHg | 1.5066 | 2860–3090, 1960, 1880, 1720, 1655, 1605, 1590, 1500, 1455, 1390, 1360, 1330, 1305, 1285, 1260, 1230, 1210, 1160, 1095, 1065, 1040, 1030, 1010, 1000, 945, 910, 850, 765, 700 |

TABLE 3-continued

| 61 | neryl angelate | | | Colorless liquid | 86° C./ 0.1 mmHg | 1.4768 | 2850-3020, 2725, 1720, 1650, 1450, 1380, 1355, 1255, 1230, 1155, 1085, 1040, 965, 845, 760, 740 |
|---|---|---|---|---|---|---|---|
| | (C$_{15}$H$_{24}$O$_2$) | | | | | | |
| 62 | furfuryl angelate | | | pale yellow liquid | 136° C./ 49 mmHg | 1.4846 | 2950-3100, 3140, 1720, 1650, 1605, 1500, 1450, 1430, 1380, 1250, 1220, 1160, 1090, 1040, 1010, 960, 920, 890, 850, 810, 740 |
| | (C$_{10}$H$_{12}$O$_3$) | | | | | | |

| Example | NMR (in CDCl$_3$, TMS Standard) H$^2$ (ppm) | C$^{13}$ (ppm) | MS (M$^+$) | Elementary Analysis (C %) | (H %) |
|---|---|---|---|---|---|
| 53 | 0.90 (t, 3H)<br>1.1-2.1 (m, 14H)<br>4.16 (t, 2H)<br>6.05 (q, 1H) | 14.03, 15.68<br>20.61, 22.78<br>31.72, 64.17<br>128.45, 137.20<br>167.81 | 184 | 71.65 | 10.73 |
| 54 | 0.88 (t, 3H)<br>1.08-1.81 (m, 12H)<br>1.87-2.04 (m, 6H)<br>4.14 (t, 2H)<br>6.02 (m, 1H) | 14.14, 15.71<br>20.64, 22.86<br>26.36, 29.01<br>29.47, 32.04<br>64.17, 128.45<br>137.20, 167.83 | 212 | 73.62 | 11.51 |
| 55 | 0.88 (t, 3H)<br>1.08-1.81 (m, 14H)<br>1.87-2.04 (m, 6H)<br>4.14 (t, 2H)<br>6.02 (m, 1H) | 14.11, 15.68<br>20.61, 22.89<br>26.36, 29.01<br>29.50, 29.77<br>32.12, 64.11<br>128.45, 137.14<br>167.70 | 226 | 74.13 | 11.63 |
| 56 | 0.88 (t. 3H)<br>1.14-1.78 (m, 16H)<br>1.87-2.04 (m, 6H)<br>4.14 (t, 2H)<br>6.03 (m, 1H) | 14.11, 15.68<br>20.59, 22.81<br>26.27, 28.93<br>29.44, 29.69<br>32.07, 64.20<br>128.37, 137.14<br>167.94 | 240 | 74.81 | 11.35 |
| 57 | 1.69-2.00 (m, 14H)<br>5.23 (m, 1H)<br>6.02 (m, 1H) | 15.63, 20.61<br>23.95, 32.99<br>76.77, 128.75<br>136.63<br>167.72 | 168 | 71.33 | 9.46 |
| 58 | 1.36-2.04 (m, 16H)<br>4.85 (m, 1H)<br>6.01 (m, 1H) | 15.68, 20.64<br>23.84, 25.73<br>31.85, 72.11<br>128.83<br>136.60<br>167.40 | 182 | 72.35 | 9.88 |
| 59 | 0.84-1.00 (m, 6H)<br>1.12-1.46 (m, 6H)<br>3.98 (m, 2H) | 14.30, 15.71<br>17.17, 20.18<br>20.64, 32.64<br>36.05, 69.07<br>128.45, 137.28<br>167.89 | 184 | 71.88 | 10.63 |
| 60 | 1.54 (d, 3H)<br>1.88-2.01 (m, 6H)<br>5.85-6.15 (m, 2H)<br>7.28-7.42 (m, 5H) | 15.70, 20.57<br>22,50, 72.04<br>126.09, 127.72<br>128.30, 128.50<br>137.42<br>142.18<br>167.07 | 204 | 76.33 | 7.65 |
| 61 | 1.60-2.14 (m, 19H)<br>4.63 (t, 2H)<br>4.95-5.23 (m, 1H)<br>5.40 (t, 1H) | 15.79, 17.72<br>20.72, 23.56<br>25.73, 26.92<br>32.45, 60.70 | 236 | 76.01 | 10.18 |

TABLE 3-continued

| | | | | | | |
|---|---|---|---|---|---|---|
| | 6.01 (m, 1H) | | 120.10, | 123.98 | | |
| | | | 128.45, | 132.02 | | |
| | | | 137.28, | 141.91 | | |
| | | | 167.86 | | | |
| 62 | 1.8–2.1 (m, 6H) | | 15.68, | 20.45 | 164 | 73.06 | 7.14 |
| | 5.14 (s, 2H) | | 57.70, | 110.38 | | |
| | 6.07 (q, 1H) | | 110.62, | 127.88 | | |
| | 4.3–4.5 (m, 2H) | | 138.25 | | | |
| | 5.40 (d, 1H) | | 143.16 | | | |
| | | | 150.25 | | | |
| | | | 167.32 | | | |

EXAMPLE 63

An example of the formulations using n-hexyl angelate: Gardenia type

| | % by weight |
|---|---|
| Heliotropin | 5.0 |
| Pentalide | 2.0 |
| Methylphenylcarbinyl acetate | 3.0 |
| cis-3-Hexenol | 1.0 |
| cis-3-Hexenyl benzoate | 3.0 |
| Ylang-ylang oil | 3.0 |
| Linalol | 15.0 |
| Linalyl acetate | 5.0 |
| Gammanonyl lactone | 2.0 |
| Hydroxycitronellal | 20.0 |
| Jasmine compound | 8.0 |
| Alpha-ionone | 10.0 |
| Cinnamic alcohol | 4.0 |
| Phenylethyl alcohol | 10.0 |
| Dimethylbenzylcarbinol | 4.0 |
| n-Hexyl angelate | 5.0 |
| Total | 100.0 |

The above-mentioned perfume composition had improved natural floral fresh feeling as compared with a reference composition with no n-hexyl angelate incorporated.

EXAMPLE 64

An example of the formulations using n-heptyl angelate: Rose muget type

| | % by weight |
|---|---|
| Linalool | 2.5 |
| Benzyl acetate | 1.5 |
| Rhodinol | 5.0 |
| Lily aldehyde | 10.0 |
| Ethylene brassylate | 5.0 |
| Hyacinth oil | 0.5 |
| Geranium oil | 1.5 |
| Geraniol | 8.0 |
| Phenylethyl alcohol | 10.0 |
| Hydroxycitronellal | 30.0 |
| Hexylcinnamaldehyde | 20.0 |
| Phenylpropyl alcohol | 0.3 |
| Indole | 0.2 |
| Petitgrain | 0.5 |
| n-Heptyl angelate | 5.0 |
| Total | 100.0 |

The above-mentioned perfume composition had emphasized floral feeling with increased rosy fragrance as compared with a reference composition with no n-heptyl angelate incorporated.

EXAMPLE 65

An example of the formulations using n-octyl angelate: Hyacinth type

| | % by weight |
|---|---|
| Hyacinth, artificial, MS | 80.0 |
| Styrax resin | 1.5 |
| Styrax essence | 0.5 |
| Indole 10% | 1.0 |
| Ylang-ylang essential oil | 1.0 |
| 5-Cyclohexadecene | 0.5 |
| Jasmine absolute | 0.1 |
| cis-3-Hexenyl salicylate | 1.4 |
| Phenylethyl alcohol | 10.0 |
| n-Octyl angelate | 4.0 |
| Total | 100.0 |

The above-mentioned perfume composition had improved brilliant, light floral feeling with increased fragrance of phenylethyl alcohol as compared with a reference composition with no n-octyl angelate incorporated.

EXAMPLE 66

An example of the formulations using n-nonyl angelate: Rose type

| | % by weight |
|---|---|
| Bulgarian rose oil | 1.0 |
| Rose absolute | 2.0 |
| Phenylethyl alcohol | 30.0 |
| Phenylethyl acetate | 7.5 |
| Linalool | 6.0 |
| Benzyl acetate | 7.5 |
| Bergamot oil | 5.0 |
| l-Citronellol | 18.5 |
| Geraniol | 20.0 |
| n-Nonyl angelate | 2.5 |
| Total | 100.0 |

The above-mentioned perfume composition had improved green-note freshness and retainability as compared with a reference composition with no n-nonyl angelate incorporated.

EXAMPLE 67

An example of the formulations using n-decyl angelate: Lilac type

| | % by weight |
|---|---|
| Cinamyl alcohol | 32.0 |
| Terpineol | 32.0 |
| Hydroxycitronellal | 10.0 |
| Benzyl acetate | 7.0 |
| Ylang-ylang oil | 6.0 |
| Phenylethyl alcohol | 11.0 |
| n-Decyl angelate | 2.0 |
| Total | 100.0 |

The above-mentioned perfume composition had improved white image of lilac and floral feeling as well as added natural feeling being more lilac-like.

EXAMPLE 68

An example of the formulations using cyclopentyl angelate: Cologne type for shampoo

|  | % by weight |
| --- | --- |
| Petigrain oil | 25.0 |
| Lemon oil, artificial | 20.0 |
| Lavandine oil | 19.0 |
| Sweet orange oil | 4.0 |
| Methylphenylcarbinyl acetate | 1.0 |
| Cinnamic alcohol | 2.0 |
| Citronellol | 5.0 |
| Dihydroterpinyl acetate | 5.0 |
| α-Amylcinnamaldehyde | 5.0 |
| Patchouli Singapore | 2.0 |
| Labdanum oil | 0.5 |
| Benzoin resin | 1.0 |
| Ethylene brassylate | 3.0 |
| 5-Cyclohexadecenone | 1.0 |
| Coumarin | 5.0 |
| Thyme oil | 0.2 |
| Aldehyde C-10 | 0.2 |
| Aldehyde C-11 | 0.1 |
| Cyclopentyl angelate | 1.0 |
| Total | 100.0 |

The above-mentioned perfume composition had improved strength and diffusibility and emphasized rose-like soft feeling as compared with a reference composition with no cyclopentyl angelate incorporated.

EXAMPLE 69

An example of the formulations using cyclohexyl angelate: Herbal type for room fresh corner

|  | % by weight |
| --- | --- |
| α-Amylcinnamaldehyde | 20.0 |
| Cedar wood oil | 20.0 |
| Phenylethyl alcohol | 15.0 |
| Amyl salicylate | 10.0 |
| Pine needle oil | 5.0 |
| Lavandine oil | 5.0 |
| Petitgrain oil | 5.0 |
| Lily aldehyde | 5.0 |
| Linalool | 4.0 |
| cis-3-Hexenol | 2.5 |
| Spearmint oil 10% (in triethyl citrate) | 2.0 |
| Lavandine absolute | 1.5 |
| 5-Cyclohexadecene | 1.5 |
| Sandiol | 1.0 |
| Cedar leef oil | 0.5 |
| cis-3-Hexenyl acetate | 0.5 |
| Methyl dihydrojasmonate | 0.5 |
| Cyclohexyl angelate | 1.0 |
| Total | 100.0 |

The above-mentioned perfume composition had emphasized fresh, soft floral green note as compared with a reference composition with no cyclohexyl angelate incorporated.

EXAMPLE 70

An example of the formulations using α-methylbenzyl sngelate: Orchid type

|  | % by weight |
| --- | --- |
| Amyl salicylate | 11.0 |
| Isobutyl salicylate | 11.0 |
| Linalool | 7.0 |
| Hydroxycitronellal | 5.0 |
| Ylang-ylang oil | 8.0 |
| Heliotropin | 3.0 |
| Coumarin | 1.0 |
| Pentalide | 5.0 |
| 5-Cyclohexadecenone | 2.0 |
| Oak moss absolute | 0.3 |
| Vanillin | 0.7 |
| Phenylacetaldehyde | 2.0 |
| Phenylethyl alcohol | 10.0 |
| Benzyl acetate | 4.0 |
| Neroli oil | 3.0 |
| Anisaldehyde | 2.0 |
| Methylionone | 10.0 |
| α-Methylbenzyl angelate | 15.0 |
| Total | 100.0 |

The above-mentioned perfume composition had improved floral feeling as compared with a reference composition with no α-methylbenzyl angelate incorporated.

EXAMPLE 71

An example of the formulations using neryl angelate: Fancy rose type

|  | % by weight |
| --- | --- |
| Rose P | 20.0 |
| Geraniol | 5.0 |
| Citronellol | 10.0 |
| Nerol | 3.0 |
| Hydroxycitronellal | 2.0 |
| Rhodinol | 28.0 |
| Rose essence | 1.0 |
| Guaiac wood oil | 5.0 |
| Rose phenone | 1.0 |
| Benzyl alcohol | 2.0 |
| Benzyl acetate | 3.5 |
| Linalool | 3.0 |
| Geranium Bourbon | 1.0 |
| Methylphenylcarbinyl acetate | 0.5 |
| Heliotropin | 1.0 |
| Coumarin | 2.0 |
| Pentalide | 1.0 |
| β-Ionone | 5.0 |
| Benzyl salicylate | 4.0 |
| Neryl angelate | 5.0 |
| Total | 100.0 |

The above-mentioned perfume composition had increased body and sweetness and better floral fragrance as compared with a reference composition with no neryl angelate incorporated.

EXAMPLE 72

An example of the formulations using furfuryl angelate:

|  | % by weight |
| --- | --- |
| Bergamot oil | 30.0 |
| Clove vanillin | 5.0 |
| Coumarin | 8.0 |
| Santalol | 8.0 |
| Vetiverol | 6.0 |
| Musk ketone | 3.5 |
| Musk ambrette | 2.5 |
| Myrrh resinoid | 5.0 |
| Castoreum absolute | 0.5 |
| Benzoin resinoid | 5.0 |
| Tall resinoid | 4.0 |

-continued

|  | % by weight |
|---|---|
| α-Ionone | 3.0 |
| Linalyl acetate | 4.0 |
| Olibanum resinoid | 3.5 |
| Furfuryl angelate | 5.0 |
| Total | 100.0 |

The above-mentioned perfume composition had improved light and fresh feeling as compared with a reference composition with no furfuryl angelate incorporated.

EXAMPLE 73

Preparation of Amyl Angelate

A mixture of 80.0 g. of methyl angelate, 65.0 g. of amyl alcohol, 200 ml. of toluene and 4.0 g. of dioctyl laurate was placed in a glass flask, which was equipped with a Soxhlet extractor filled on the top with molecular sieve 4A and a reflux cooler. The above mixture was heated under continuous reflux while returning the refluxed liquid through the molecular sieve 4A to the flask. The mixture resulted from the heating for a total of 24 hours was subjected to single distillation to give 98.3 g. of a distillate boiling at 85°–100° C. (30 mmHg). The distillate was further subjected to rectification to give 64.8 g. of a distillation boiling at 94° C. (30 mmHg). Analysis of the compound by gaschromatography (Capillary column: 25 m×0.3 mmϕ PEG 20M) indicated a purity of 99.3% in terms of the area ratio.

Refractive index (D ray, 20° C.) was 1.4375. Infrared spectrum had absorptions at 2860–3020, 1720, 1650, 1455, 1390, 1380, 1350, 1260, 1230, 1160, 1085, 1045, 975, 845, 760 and 730 cm$^{-1}$ (liquid film).

Proton nuclear magnetic resonance spectrum (deuterochloroform, TMS internal standard) had absorptions at δ=13.98, 15.68, 20.61, 22.51, 28.50, 28.66, 64.20, 128.45, 137.17 and 168.00.

Organic elementary analysis indicated C=70.31% and H=10.39%.

EXAMPLES 74–79

Esters of angelic acid with other alcohols were prepared in the same way as in Example 73. Physical properties and analytical values were shown in Table 4.

TABLE 4

| Example | Angelate (structural formula, molecular formula) | Characteristics | Boiling Point | Refraction Index ($n_D^{20}$) | IR (cm$^{-1}$) |
|---|---|---|---|---|---|
| 74 | 2-methylpropenyl angelate ($C_9H_{14}O_2$) | Colorless liquid | 90° C./ 32 mmHg | 1.4527 | 3070, 2885–3050, 1720, 1660, 1450, 1380, 1350, 1260, 1230, 1150, 1090, 1040, 990, 960, 900, 850, 760 |
| 75 | 2-methylbutyl angelate ($C_{10}H_{18}O_2$) | Colorless liquid | 98° C./ 26 mmHg | 1.4391 | 2850–3050, 1720, 1650, 1460, 1390, 1350, 1260, 1230, 1160, 1090, 1040, 990, 850, 760 |
| 76 | benzyl angelate ($C_{12}H_{14}O_2$) | Colorless liquid | 92° C./ 2 mmHg | 1.5148 | 2850–3120, 2725, 1960, 1880, 1800, 1720, 1650, 1605, 1585, 1500, 1450, 1385, 1350, 1255, 1230, 1140, 965, 800, 760, 730, 700, 675 |
| 77 | β-phenylethyl angelate ($C_{13}H_{16}O_2$) | Colorless liquid | 84° C./ 0.5 mmHg | 1.5103 | 2860–3090, 1720, 1655, 1605, 1500, 1455, 1390, 1355, 1260, 1235, 1160, 1085, 1045, 995, 850, 755, 700 |

TABLE 4-continued

| | | | | | |
|---|---|---|---|---|---|
| 78 | gelamyl angelate (C₁₅H₂₄O₂) | Colorless liquid | 102° C./ 1.2 mmHg | 1.4773 | 2860–3020, 1720, 1655, 1450, 1385, 1355, 1255, 1230, 1155, 1085, 1040, 960, 850, 760 |
| 79 | citronellyl angelate (C₁₅H₂₆O₂) | Colorless liquid | 105° C./ 0.5 mmHg | 1.4616 | 2850–3020, 1720, 1655, 1460, 1385, 1355, 1260, 1230, 1060, 1085, 1045, 980, 850, 760 |

| Example | NMR (ppm) (in CDCl₃, TMS Standard) H¹ | C¹³ | MS (M⁺) | Elementary Analysis C (%) | H (%) |
|---|---|---|---|---|---|
| 74 | 1.80 (s, 3H) 1.9–2.1 (m) 4.59 (s, 2H) 4.96 (d, 2H) 6.10 (m, 1H) | 15.74, 19.58 20.59, 67.42 112.74, 128.12 137.93 140.37 167.48 | 154 | 70.06 | 9.23 |
| 75 | 0.93 (d, 3H) 0.8–2.10 (m, 12H) 4.02 (m, 2H) 6.04 (m, 1H) | 11.30, 15.71 16.69, 20.64 26.44, 34.51 68.77, 128.45 137.28 167.97 | 170 | 70.34 | 10.44 |
| 76 | 1.89–2.02 (m, 6H) 5.18 (s, 2H) 6.02 (m, 1H) 7.20–7.40 (m, 5H) | 15.72, 20.53 65.80, 127.99 128.50, 136.50 137.96 167.65 | 190 | 75.68 | 7.33 |
| 77 | 1.82–1.96 (m, 6H) 2.95 (t, 2H) 4.34 (t, 2H) 5.90 (m, 1H) 7.17–7.39 (m, 5H) | 15.66, 20.53 35.32, 64.58 126.52, 128,04 128.47, 128.76 137.68 138.17 167.51 | 204 | 76.29 | 7.77 |
| 78 | 1.60–2.06 (m, 19H) 4.66 (d, 2H) 5.08 (m, 1H) 5.40 (t, 1H) 6.01 (m, 1H) | 15.68, 16.44 17.66, 20.64 25.65, 26.52 39.68, 60.89 119.24, 124.03 128.42, 131.56 137.09, 141.61 167.81 | 236 | 76.03 | 10.01 |
| 79 | 0.93 (d, 2H) 1.11–2.12 (m, 19H) 4.19 (t, 1H) 5.09 (m, 1H) 6.02 (m, 1H) | 15.65, 17.63 19.53, 20.55 25.52, 25.65 29.74, 35.76 37.13, 62.58 124.72, 128.35 131.23, 137.06 168.09 | 238 | 75.51 | 10.81 |

EXAMPLE 80

An example of the formulations using 2-methylpropenyl angelate: Rose type

| | % by weight |
|---|---|
| Phenylethyl alcohol | 50.0 |
| Rhodinol pure | 20.0 |
| Geranium oil | 6.0 |
| Geranyl acetate | 4.0 |
| Nerol | 3.0 |
| Trichloromethylphenylcarbinyl acetate | 2.5 |
| Phenylethyl acetate | 2.5 |
| Hydroxycitronellal | 2.0 |
| Methyleugenol | 2.0 |
| Undecylaldehyde 10% (in triethyl citrate) | 2.0 |
| Palmarosa oil | 2.0 |
| Guaiacyl acetate | 1.5 |
| Citral | 1.0 |
| Dimethylbenzylcarbinyl acetate | 1.0 |
| 2-Methylpropenyl angelate | 0.5 |
| Total | 100.0 |

The above-mentioned perfume composition had improved natural and diffusible green floral feeling as compared with a reference composition with no 2-methylpropenyl angelate incorporated.

EXAMPLE 81

An example of the formulations using n-amyl angelate: Fragrant olive type

|  | % by weight |
|---|---|
| Ethyl caprate | 1.0 |
| Linalool | 10.0 |
| Benzyl acetate | 10.0 |
| Methyl ionone | 5.0 |
| Ethyl butyrate | 0.5 |
| Amyl acetate | 1.0 |
| Benzaldehyde | 0.3 |
| Phenylethyl acetate | 3.0 |
| Geranyl acetate | 1.0 |
| Anethole | 1.0 |
| β-Pinene | 10.0 |
| γn-Decalactone | 6.0 |
| Benzyl propionate | 5.0 |
| Phenylethyl alcohol | 10.0 |
| Amylcinnamaldehyde | 5.0 |
| Dihydromyrcenol | 0.5 |
| Phenylethyl isobutyrate | 10.0 |
| Geraniol | 5.0 |
| Linalyl acetate | 5.0 |
| Hydroxycitronellal | 5.0 |
| Indole | 0.2 |
| Ethyl caproate | 0.5 |
| n-Amyl angelate | 5.0 |
| Total | 100.0 |

The above-mentioned perfume composition had emphasized lactone-like sweetness and improved floral feeling as compared with a reference composition with no n-amyl angelate incorporated.

EXAMPLE 82

An example of the formulations using 2-methylbutyl angelate: Floral bouquet type

|  | % by weight |
|---|---|
| Hexylcinnamaldehyde | 25.0 |
| Hydroxycitronellal | 15.0 |
| Rhodinol | 10.0 |
| Tetrahydrolinalol | 7.0 |
| Benzyl salicylate | 6.0 |
| Indole 10% (in triethyl citrate) | 5.0 |
| Hexyl salicylate | 5.0 |
| Lily aldehyde pure | 5.0 |
| Benzyl acetate | 5.0 |
| Linalool | 3.0 |
| Ylang-ylang oil extra | 2.5 |
| Sandeol | 2.5 |
| Cinnamic alcohol | 2.5 |
| Geranium oil | 1.5 |
| 2-Methylbutyl angelate | 5.0 |
| Total | 100.0 |

The above-mentioned perfume composition had improved natural and elegant floral feeling as compared with a reference composition with no 2-methylbutyl angelate incorporated.

EXAMPLE 83

An example of the formulations using benzyl angelate: Tulip type

|  | % by weight |
|---|---|
| Benzylphenyl acetate | 30.0 |
| Coumarin | 5.0 |
| Dimethylhydroquinone | 3.0 |
| Geraniol | 6.0 |
| Nerol | 3.0 |
| Citronellol | 8.0 |
| Phenylethyl alcohol | 10.0 |
| Phenylethyl acetate | 5.0 |
| Ionone pure | 5.0 |
| Normalbutyl acetate | 5.0 |
| Guaiac wood oil | 10.0 |
| Geranium oil | 1.0 |
| Benzaldehyde | 1.0 |
| Aldehyde $C_{14}$ 100% | 1.0 |
| Benzyl angelate | 7.0 |
| Total | 100.0 |

The above-mentioned perfume composition had improved fresh floral and natural feeling as compared with a reference composition with no benzyl angelate incorporated.

EXAMPLE 84

An example of the formulations using β-phenylethyl angelate: Rose type

|  | % by weight |
|---|---|
| Geraniol | 15.0 |
| Citronellol | 20.0 |
| Phenylethyl alcohol | 50.0 |
| Geranyl acetate | 3.0 |
| Geranyl butyrate | 1.0 |
| Guaiac wood oil | 6.0 |
| Aldehyde C-11 | 0.5 |
| Phenylacetic acid 10% | 0.5 |
| Geranium bourbon oil | 3.5 |
| β-Phenylethyl angelate | 0.5 |
| Total | 100.0 |

The above-mentioned perfume composition had improved fresh and natural feeling as compared with a reference composition with no β-phenylethyl angelate incorporated.

EXAMPLE 85

An example of the formulations using geranyl angelate: Rose type

|  | % by weight |
|---|---|
| Phenylethyl alcohol | 47.0 |
| Geraniol | 12.0 |
| Citronellol | 18.0 |
| Geranium S.B.S. | 1.5 |
| Phenylethyl formate | 0.5 |
| Nerol | 6.5 |
| Phenylethyl acetate | 3.5 |
| Nerolidol | 1.5 |
| Phenylethyl phenylacetate | 5.5 |
| Phenylethyl salicylate | 2.5 |
| Geranyl angelate | 1.0 |
| Total | 100.0 |

The above-mentioned perfume composition had improved sweetness of Bulgarian rose and fresh and acceptable blue feeling as well as emphasized fragrance of rose as compared with a reference composition with no geranyl angelate incorporated.

EXAMPLE 86

An example of the formulations using citronellyl angelate: Fusea for soap

|  | % by weight |
| --- | --- |
| Lavender oil | 20.0 |
| Bergamot oil, artificial | 15.0 |
| Geranium oil | 10.0 |
| p-tert-Butylcyclohexyl acetate | 10.0 |
| Terpeniol | 7.5 |
| Coumarin | 7.0 |
| Tetrahydrolinalol | 5.0 |
| Amyl salicylate | 5.0 |
| Lily aldehyde pure | 5.0 |
| Linalyl acetate | 5.0 |
| Sandeol | 4.0 |
| Absolute tree moss | 1.5 |
| Citronellyl angelate | 5.0 |
| Total | 100.0 |

The above-mentioned perfume composition had improved natural, mild and rose-like note as compared with a reference composition with no citronellyl angelate incorporated.

COMMERCIAL UTILITY

As described above, according to the present invention angelic acid and esters thereof which are useful as perfume materials are prepared at a low cost, and novel perfume materials heretofore unknown are also provided.

We claim:

1. Process for preparing angelic acid or esters thereof which comprises isomerizing tiglic acid or an ester thereof in the presence of an organic sulfinic acid to form a thermal equilibrium mixture in which the content of angelic acid or ester is less than the content of tiglic acid or ester, and distilling angelic acid or ester from the mixture.

2. Process according to claim 1 wherein the ester of tiglic acid is a lower alkyl ester of tiglic acid.

3. Process according to claim 1 wherein the ester of tiglic acid is methyl tiglate.

4. Process according to any one of claims 1-3 wherein the organic sulfinic acid is an arylsulfinic acid or an alkylsulfinic acid.

5. Process according to claim 1 wherein the isomerization reaction is carried out at a temperature in the range from room temperature to 200° C.

6. The process according to any one of claims 1-3 wherein the organic sulfinic acid is an arylsulfinic acid or an alkylsulfinic acid and the isomerization reaction is carried out at a temperature in the range from room temperature to 200° C.

7. The process of claim 1 in which the product is an ester of angelic acid represented by the formula

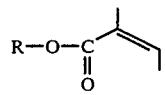

wherein R represents 3-hexenyl, 3-methyl-2-butenyl, 3-methyl-3-butenyl, 3-methyl-2-pentenyl, 3-methyl-4-pentenyl, $CH_3(CH_2)_l$-(in which l is an integer from 5 to 9), cyclopentyl, cyclohexyl, 2-methylpentyl, α-methylbenzyl, neryl or furfuryl.

8. Process for preparing an ester of angelic acid represented by the formula

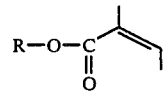

wherein R represents 3-hexenyl, 3-methyl-2-butenyl, 3-methyl-3-butenyl, 3-methyl-2-pentenyl, 3-methyl-4-pentenyl, $CH_3(CH_2)_l$-(in which l is an integer from 5 to 9), cyclopentyl, cyclohexyl, 2-methylpentyl, α-methylbenzyl, neryl or furfuryl comprising preparing methyl angelate by the process of claim 1, followed by transesterification using ROH.

9. Process for preparing an ester of angelic acid represented by the formula (II)

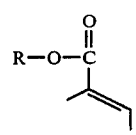

(II)

wherein R is selected from the group consisting of alkyl having 1-10 carbon atoms, alkenyl having 2-10 carbon atoms, cycloalkyl having not more than 10 carbon atoms α-phenylethyl, β-phenylethyl, benzyl or furfuryl, comprising preparing methyl angelate according to the process of claim 1, followed by transesterifying the resulting ester using ROH.

10. Process for preparing angelic acid or an ester thereof comprising isomerizing tiglic acid or an ester thereof represented by the formula (I)

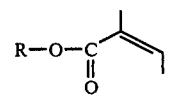

(I)

wherein R is selected from the group consisting of H, alkyl having 1-10 carbon atoms, alkenyl having 2-10 carbon atoms, cycloalkyl having not more than 10 carbon atoms, α-phenylethyl, β-phenylethyl, benzyl or furfuryl, in the presence of an organic sulfinic acid selected from the group consisting of alkyl sulfinic acid having 1-20 carbon atoms, p-toluenesulfinic acid, benzenesulfinic acid, chlorobenzensulfinic acid, and β-naphthalenesulfinic acid; and distilling the resulting angelic acid or ester thereof from the tiglic acid or ester thereof.

11. Process for preparing angelic acid or esters thereof according to the formula (II)

(II)

wherein R is selected from the group consisting of H, alkyl having 1-10 carbon atoms, alkenyl having 2-10 carbon atoms, cycloalkyl having not more than 10 carbon atoms, α-phenylethyl, β-phenylethyl, benzyl or furfuryl; comprising (a) isomerizing at a temperature range from about room temperature to about 200° C., tiglic acid or an ester thereof represented by the formula (I)

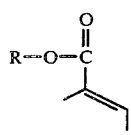

(I)

wherein R is selected from the group consisting of H, alkyl having 1-10 carbon atoms, alkenyl having 2-10 carbon atoms, cycloalkyl having not more than 10 carbon atoms, α-phenylethyl, β-phenylethyl, benzyl or furfuryl, in the presence of an organic sulfinic acid selected from the group consisting of alkyl sulfinic acid having 1-20 carbon atoms, p-toluenesulfinic acid, benzenesulfinic acid, chlorobenzenesulfinic acid and β-naphthalenesulfinic acid;

(b) continuously removing said angelic acid or ester thereof by distillation; and (c) transesterifying said angelic acid ester by reacting with ROH.

* * * * *